United States Patent
Stevenson et al.

(10) Patent No.: US 6,602,519 B1
(45) Date of Patent: Aug. 5, 2003

(54) OXIDIZED THYMOSIN β4

(75) Inventors: Robert Duncan Stevenson, Ardinning, Moor Road, Strathblane G63 9EX (GB); Anthony John Lawrence, Glasgow (GB); John Young, Larkhall (GB); Darryl John Cecil Pappin, Herts (GB)

(73) Assignees: The University Court of the University of Glasgow, Glasgow (GB); Imperial Cancer Research Technology, London (GB); Robert Duncan Stevenson, Strathblane (GB)

(*) Notice: Subject to any disclaimer, the term of this patent is extended or adjusted under 35 U.S.C. 154(b) by 0 days.

(21) Appl. No.: 09/647,117

(22) PCT Filed: Mar. 29, 1999

(86) PCT No.: PCT/GB99/00833
§ 371 (c)(1),
(2), (4) Date: Jan. 23, 2001

(87) PCT Pub. No.: WO99/49883
PCT Pub. Date: Oct. 7, 1999

(30) Foreign Application Priority Data

Mar. 28, 1998 (GB) ............................................. 9806632

(51) Int. Cl.⁷ ................................................. A61K 9/48
(52) U.S. Cl. ........................ 424/451; 424/464; 424/489; 424/422; 424/434; 424/435; 424/436; 514/2; 514/12
(58) Field of Search ................................ 424/400, 422, 424/430, 435, 436, 451, 464, 489, 434; 514/2, 12

(56) References Cited

U.S. PATENT DOCUMENTS 4,388,234 A   6/1983   Horecker ................. 260/112.5
4,389,343 A   6/1983   Horecker ................. 260/112.5 R
5,578,570 A * 11/1996  Goldstein et al. ............. 514/12
5,593,964 A *  1/1997  Goldstein et al. ............. 514/12

OTHER PUBLICATIONS

Huff et al., *Interactions of β–Thymosins, Thymosinβ₄–Sulfoxide, and N–Terminally Truncated Thymosinβ₄ With Actin Studied by Equilibrium Centrifgation, Chemical Cross–Linking and Viscometry*, Eur. J. Biochem., 230, 1995, pp. 650–657.

Heintz et al., *The Sulfoxide of Thymosin β4 Almost Lacks the Polymerization–Inhibiting Capacity for Actin*, Eur. J. Biochem, 223, 1994, pp. 345–350.

Jean et al., *Interaction of G–Actin With Thymosin β₄ and Its Variants Thymosinβ₉ and Thymosinβ₉$^{met}$*, Journal of Muscle Research and Cell Motility, 15, 1994, pp. 278–286.

Hannappel et al., *Actin–Sequestering Ability of Thymosin β₄, Thymosinβ₄ Fragments, and Thymosinβ₄–Like Peptides as Assessed by the DNase I Inhibition Assay*, Biol. Chem Hoppe–Seyler, vol. 374, Feb. 1993, pp. 117–122.

Hannappel et al., *Actin–Sequestering Ability of Thymosin B₄, Thymosin B₄ Fragments, and Thymosin B₄–Like Peptides as Assesed by the DNase I Inhibition Assay*, Biological Chemistry Hoppe–Seyler, vol. 374, Feb. 1993 (1993) pp. 117–122.

International Search Report, PCT/GB 99/00833, dated Oct. 25, 1999.

\* cited by examiner

*Primary Examiner*—Thurman K. Page
*Assistant Examiner*—Liliana Di Nola-Baron
(74) *Attorney, Agent, or Firm*—Myers Bigel Sibley & Sajovec, PA

(57) ABSTRACT

The present invention relates to the use of oxidized thymosin β4 in therapy, more particularly in the treatment of diseases or conditions associated with an inflammatory response of septic shock.

4 Claims, 14 Drawing Sheets

PEPTIDE 1 : [M+2H] 2 + ION AT 1035.1 Da, COFF at -25V

N-TERMINAL : ACETYL     C-TERMINAL : FREE ACID

Figure 1:
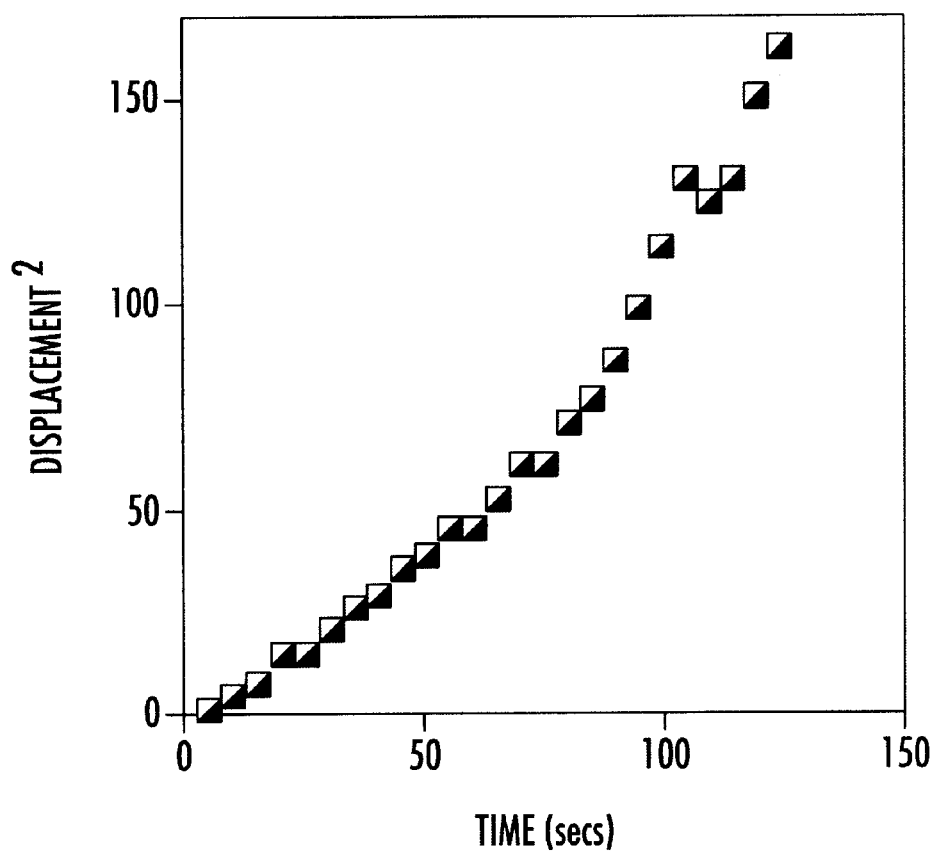

| No. | Seq | A | A-NH3 | B | B-NH3 | Y | Y-NH3 | No. |
|---|---|---|---|---|---|---|---|---|
| 1 | Ser | 102.1 | 85.0* | 130.1* | 113.0 | 2025.9 | 2008.9 | 14 |
| 2 | Asp | 217.1* | 200.1* | 245.1* | 228.1* | 1938.9 | 1921.8 | 13 |
| 3 | Kpy | 464.2* | 447.2* | 492.2* | 475.2* | 1823.8* | 1806.8 | 12 |
| 4 | Pro | 561.3* | 544.2* | 589.3* | 572.2* | 1576.7* | 1559.7* | 11 |
| 5 | Asp | 676.3* | 659.3* | 704.3* | 687.3* | 1479.6* | 1462.6 | 10 |
| 6 | Mso | 823.3* | 806.3* | 851.3* | 834.3 | 1364.6* | 1347.6 | 9 |
| 7 | Ala | 894.4* | 877.3* | 922.4* | 905.3* | 1217.6* | 1200.6* | 8 |
| 8 | Glu | 1023.4 | 1006.4 | 1051.4* | 1034.4* | 1146.5* | 1129.5 | 7 |
| 9 | Xle | 1136.5* | 1119.5 | 1164.5* | 1147.5* | 1017.5* | 1000.5 | 6 |
| 10 | Glu | 1265.5* | 1248.5* | 1293.5* | 1276.5* | 904.4* | 887.4* | 5 |
| 11 | Kpy | 1512.7* | 1495.6 | 1540.7* | 1523.6 | 775.4* | 758.4 | 4 |
| 12 | Phe | 1659.7* | 1642.7 | 1687.7* | 1670.7* | 528.2* | 511.2* | 3 |
| 13 | Asp | 1774.8* | 1757.7 | 1802.8 | 1785.7 | 381.2* | 364.2* | 2 |
| 14 | Kpy | 2021.9 | 2004.9 | 2049.9 | 2032.9 | 266.2* | 249.1 | 1 |

OXIDIZED THYMOSIN β4

The present invention relates to a peptide factor isolated from steroid-treated monocytes. More particularly the invention relates to a peptide factor which can be used to replace steroid therapy.

Steroids are effectively used for anti-inflammatory diseases, such as asthma, eczema, allergic reactions, and rheumatic diseases such as rheumatoid arthritis. However, steroids have serious side effects and are therefore only used in cases where non-steroidal anti-inflammatory drugs are not effective.

Monocytes are important immune effector cells that play a fundamental role in cellular immunity. In addition to their antigen-presenting and phagocytic activities at the sites of inflammation, peripheral blood mononuclear cells are also involved in the synthesis and release of a variety of pro-inflammatory enzymes and polypeptide cytokines which modulate neutrophil responses. The production of these components can be suppressed by glucocorticoids and this has been suggested as the basis for their anti-inflammatory action.

The effect of steroid-induced factors on neutrophil migration is primarily of interest in elucidating anti-inflammatory mechanisms. Corticosteroids down regulate the synthesis of many pro-inflammatory mediators (Lew et al 1988; Almawi et al 1991; Standford et al 1992) but some of their actions can be interpreted in terms of up-regulation of anti-inflammatory mediators.

The neutrophil migration stimulating activity of steroid induced factors suggests that dispersive locomotion tends to prevent cells collecting at a focus and this may be important in terminating inflammatory responses.

Stevenson (1973, 1974, 1978) demonstrated that human monocytes when incubated in the presence of antiinflammatory corticosteroids released a protease sensitive factor that enhanced the migration of neutrophils from a cell pellet contained in a short capillary tube.

Later studies demonstrated that the phenomenon of stimulated neutrophil migration was also observed with leucocytes from patients receiving steroid therapy.

Recently, Chettibi et al (1993, 1994) have investigated the steroid induced stimulatory effect on neutrophil migration using an automated cell tracking assay enabling study of the behaviour of cells migrating on protein-coated glass coverslip.

These Studies Determined:
1. Steroid-treated monocyte supernatant (STMS) causes a dramatic increase in the speed of locomotion of human neutrophils and a significant decrease in their adhesion to protein-coated glass. In contrast, control monocyte supernatants have a smaller effect on the speed of locomotion, but cause a large increase in adhesiveness.
2. The supernatant activity was produced equally well in the presence or absence of serum after 24 h culture at 37° C. with $10^{-6}$M dexamethasone.
3. The effect of the steroid-treated monocyte supernatant on the speed of locomotion of human peripheral blood neutrophils was not altered by rabbit polyclonal antisera against lipocortins 1–6.
4. Rabbit anti-interleukin-8 antibody which blocked the effect of IL-8 on the speed of locomotion of neutrophils did not antagonize the locomotion stimulating action of steroid-treated monocyte supernatant.
5. The exocellular release of this factor(s) by human mononuclear leucocytes suggests that it may be an in vivo mediator of the anti-inflammatory effect of glucocorticoids.

However, there is no disclosure of what the active agent(s) in STMS might be.

Huff T. et al. (1995) and Heintz D. et al. (1994) describe studies involving beta-thymosins and how they interact with G-actin in a biomolecular complex and inhibit the polymerisation to F-actin under high salt conditions. The oxidised form of thymosin β4 is disclosed as inhibiting actin polymerisation, however, only at a 20-fold higher concentration than thymosin β4. Neither document however implicates any medical role for oxidised thymosin β4. In fact the papers appear to teach away from a positive role for oxidised thymosin β4.

U.S. Pat. No. 5,578,570 (Goldstein et al.) discloses a method of treating septic shock by administering thymosin β4. There is no disclosure however of oxidised thymosin β4 or suggestion that this may have a role in treating septic shock.

It is an object of the present invention to provide a replacement to steroid therapy.

The present invention is based in part on the observations by the present inventors that the factor associated with neutrophil locomotion is an oxidised form goof thymosin β4.

According to a first aspect the present invention provides use of oxidised thymosin β4 or physiologically active variant thereof in therapy.

Typically oxidised thymosin β4 is a form of thymosin β4 in which a methionine residue, 6 amino acids from the N-terminus, (Met6), is oxidised such that the residue is converted to methionine sulphoxide. Moreover, the methionine residue (Met6) may be further oxidised to the methionine sulphone and this as such is also encompassed by the present invention. Other modifications of the methionine residue may also be evisaged, such as complexing the sulphur with metals, which may result in an active form of thymosin β4 similar to the oxidised form described herein.

It is understood that the oxidised thymosin β4 may be obtained for example by reacting native thymosin β4 under oxidising conditions, for example by treating with hydrogen peroxide, to form oxidised thymosin β4. Thus native thymosin β4 may first be obtained and thereafter oxidised to the oxidised form.

It has been observed that samples of native thymosin β4 may contain low levels, such as 10%, of oxidised thymosin β4 thought to be as a result of auto-oxidation. The present inventors however are the first to associate the oxidised form of thymosin β4 with a physiological activity. Generally speaking therefore the present invention provides the use of purified oxidised thymosin β4. Typically the present invention provides use of preparations of purified oxidised thymosin β4 which comprise at least 30%, preferably 60%, more preferably 80%, most preferably 90%, oxidised thymosin β4 with the residual portion accounting for non-oxidised thymosin β4. Preferably however the preparations of oxidised thymosin β4 comprise substantially all oxidised thymosin β4 (ie. substantially no non-oxidised thymosin β4).

Thymosin β4 in an oxidised or non-oxidised form may be obtained from any suitable source, for example from steroid treated monocytes. Moreover, the thymosin β4 may be derived from any suitable species, but is typically of mammalian origin, such as bovine, equine, murine or human origin. It is to be noted that bovine, equine, murine, rat and human thymosin β4 are all identical in sequence. Thus, for example, bovine thymosin β4 may provide a suitable source of thymosin β4 for subsequent oxidation and administration to other species, such as humans.

It is understood that physiologically active variants of the oxidised thymosin β4 are variants which display the same or similar physiological properties as the oxidised thymosin β4. It is to be preferred that such variants would include the oxidised methionine, but may be truncated, deleted or mutated forms thereof.

It will be understood that for the particular oxidised thymosin β4 embraced herein, variations (natural or otherwise) can exist. These variations may be demonstrated by (an) amino acid difference(s) in the overall sequence or by deletions, substitutions, insertions, inversions or additions of (an) amino acid(s) in said sequence. All such derivatives are included within the scope of this invention provided that the derivatives are physiologically active (ie. display oxidised thymosin β4 activity as defined herein). For example, for the purpose of the present invention conservative replacements may be made between amino acids, within the following groups:

(I) alanine, serine and threonine;

(II) glutamic acid and aspartic acid;

(III) arginine and lysine;

(IV) asparagine and glutamine;

(V) isoleucine, leucine and valine;

(VI) phenylalanine, tyrosine and tryptophan.

(VII) methionine and other methionine analogues (VIII) methionine and other methionine analogues where the sulphur is replaced by Group VIB elements (e.g. Selenium, Tellurium, Polonium).

(IX) oxidised methionine and other oxidised methionine analogues (e.g. Group VIB analogues, methionine sulphoximine).

(X) methionine and other sulphur-containing amino acids (e.g. cysteine) including their oxidised analgoues.

Early molecular modelling studies suggest that the methionine residue (met-6) is at the top of one of three helices in the peptide. Molecular modelling should help identify a shorter peptide which may have the activity observed for STMS and oxidised thymosin β4 and would be a preferred molecule to use in preparing pharmaceuticals with anti-inflammatory activity.

Indeed this may assist in the development of peptide mimetics which display the same physiological function as the oxidised thymosin β4.

Moreover, it may be possible to increase the half life of oxidised thymosin β4 or physiologically active variants thereof by use of appropriate chemical modification (eg. acetylation) or use of D amino acids.

The isolated oxidised thymosin β4 may have a blocked N-terminal.

According to the present invention there is also provided a synthetic oxidised thymosin β4 comprising the peptide sequence of thymosin β4 in oxidised form or physiologically active variant thereof.

The synthetic oxidised thymosin β4 may be modified and/or amino acid substituted as described above, as long as the physiological activity remains. For example selenomethionine could be introduced in place of methionine and oxidised in the same manner.

The invention further provides the use of an oxidised peptide as described herein in the preparation of a medicament for the treatment of a chronic or acute inflammatory condition. Such inflammatory conditions include Inflammatory Arthropathies such as Rheumatoid arthritis, Psoriatic arthritis, Crystal arthritis, Reactive arthritis, Ankylosing spondylitis, Infectious arthritis, Juvenile chronic arthritis; Connective Tissue Diseases, such as Systemic Lupus Erythematosis, Sjogren's Syndrome, Polymyalgia Rheumatica, Cranial arteritis; Vasculitic Syndromes, such as Wegener's Granulomatosis, Polyarteritis Nodosa, Churg Strauss Syndrome; Respiratory Diseases, such as Asthma, Chronic Obstructive Pulmonary Disease, Fibrosing Alveolitis, Hypersensitivity Pneumonitis, Sarcoidosis, Allergic aspergillosis, Cryptogenic pulmonary eosinophilia, Bronchiolitis obliterans organising pneumonia; Dermatological Diseases, such as Inflammatory dermatosis including psoriasis, Eczema, Urticaria; Gastro-intestinal Diseases, such as Ulcerative Colitis, Crohn's Disease, Lupoid hepatitis; Haematological Disease, such as Haemolytic anaemia, Idiopathic Thrombocytopenic Purpura, Multiple Myeloma, Lymphoma/leukaemia; Transplantation/Prosthetics, such as Graft rejection, Graft versus host disease, Tissue reaction to implanted prostheses; and Infections, such as Tuberculosis, Malaria Pneumocystis carinii pneumonia, Leprosy.

Moreover, oxidised thymosin β4 may be administered in conjunction with other drugs, eg. cytokines such as interferon which may induce an inflammatory response as a side effect. Thus, in one aspect oxidised thymosin β4 may serve to minimise or reduce physiological or disease states which are characterised in part by inappropriate inflammation.

Additionally, it should be appreciated that the uses of oxidised thymosin β4 mentioned above do not only extend to human conditions. Thus, oxidised thymosin β4 may be used in the treatment of animals such as cats, dogs, horses, cows, sheep, pigs and goats with similar conditions to those mentioned above.

The present invention further provides the use of oxidised thymosin β4 in the preparation of a medicament for the treatment of septic shock. Typically the oxidised thymosin β4 is in a purified form as described above.

The invention further provides a pharmaceutical composition comprising oxidised thymosin β4 as described herein.

The invention further provides use of a nucleotide molecule having a sequence capable of encoding thymosin β4 as described herein for subsequently preparing oxidised thymosin β4.

In a particular embodiment the invention provides the use of a vector or vectors comprising the nucleotide molecule in the preparation of oxidised thymosin β4 and trancated, deleted and mutated forms thereof as described herein.

Alternatively the present invention provides the use of a vector or vectors comprising the nucleotide molecule in the preparation of a medicament comprising oxidised thymosin β4 and trancated, deleted and mutated forms thereof for the treatment of a inflammatory condition.

The use of oxidised thymosin β4 as described herein in place of steroid treatment will alleviate the side effects which are normally associated with the use of steroids.

The oxidised thymosin β4 can be used for treatment of patients where non steroidal anti inflammatory drugs are currently used as an alternative to steroids because of the risks of side-effects.

Use of highly purified oxidised thymosin β4 or of synthetic or expressed thymosin β4 which is subsequently oxidised will be safe and reliable, since it will generally not be foreign to the body to which it is being administered.

Accurate amounts can be administered.

The amount of oxidised thymosin β4 required to be effective in a treatment will, of course, vary and is ultimately at the discretion of the medical or veterinary practitioner. The factors to be considered include the condition being treated, the route of administration, and nature of the formulation, the recipients body weight, surface area, age and general condition, and the particular compound to be administered. A suitable effective dose may lie in the range of about 0.001 to about 120 mg/kg bodyweight, e.g. 0.01 to about 120 mg/kg body weight, preferably in the range of about 0.01 to 50 mg/kg, for example 0.05 to 20 mg/kg. The total daily dose may be given as a single dose, multiple doses, e.g., two to six times per day or by intravenous infusion for selected duration. For example, for a 75 kg mammal (e.g. a human) the dose range may be about 8 to 9000 mg per day, and a typical dose could be about 50 mg per day. If discrete multiple doses are indicated treatment might typically be 15 mg of oxidised thymosin β4 given up to 4 times per day.

Whilst it is possible for the active compound to be administered alone, it is preferable to present the active compound in a pharmaceutical formulation. Formulations of the present invention, for medical use, comprise oxidised thymosin β4, or a salt thereof together with one or more pharmaceutically acceptable carriers and optionally other therapeutic ingredients. The carrier(s) should be pharmaceutically acceptable in the sense of being compatible with the other ingredients of the formulation and not deleterious to the recipient.

The present invention, therefore, further provides a pharmaceutical formulation comprising oxidised thymosin β4 or a pharmaceutically acceptable salt or physiologically functional derivative thereof together with a pharmaceutically acceptable carrier therefor.

There is also provided a method for the preparation of a pharmaceutical formulation comprising bringing into association oxidised thymosin β4 or a pharmaceutically acceptable salt or physiologically functional derivative thereof, and a pharmaceutically acceptable carrier therefor.

Formulations according to the present invention include those suitable for oral, nasal, topical, vaginal, rectal or parenteral (including subcutaneous, intraarthrodial (ie. within joints) intramuscular and intravenous) administration including biolistic eg. Powderject® administration. Preferred formulations are those suitable for oral, topical or parenteral administration.

The formulations may conveniently be presented in unit dosage form and may be prepared by any of the methods well known in the art of pharmacy. All methods include the step of bringing the active compound into association with a carrier which constitutes one or more accessory ingredients. In general, the formulations are prepared by uniformly and intimately bringing the active compound into association with a liquid carrier or a finely divided solid carrier or both and then, if necessary, shaping the product into desired formulations.

Formulations of the present invention suitable for oral administration may be presented as discrete units as capsules, cachets, tablets, lozenges, comprising the active ingredient in a flavoured base, usually sucrose and acacia or tragacanth; pastilles comprising the active ingredient in an inert base such as gelatin and glycerin, or sucrose and acacia; and mouth-washes comprising the active ingredient in a suitable liquid carrier. Each formulation generally contains a predetermined amount of the active compound; as a powder or granules; or a solution or suspension in an aqueous or non-aqueous liquid such as a syrup, an elixir, an emulsion or draught and the like.

A tablet may be made by compression or moulding, optionally with one or more accessory ingredients. Compressed, tablets may be prepared by compressing in a suitable machine the active compound in a free-flowing form such as a powder or granules, optionally mixed with a binder, (e.g. povidone, gelatin, hydroxypropylmethyl cellulose), lubricant, inert diluent, preservative, disintegrant (e.g. sodium starch glycollate, cross-linked povidone, cross-linked sodium carboxymethyl cellulose), surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethylcellulose in varying proportions to provide the desired release profile.

A syrup may be made adding the active compound to a concentrated, aqueous solution of a sugar, for example sucrose, to which may also be added any accessory ingredients. Such accessory ingredient(s) may include flavourings, an agent to retard crystallization of the sugar or an agent to increase the solubility of any other ingredients, such as a polyhydric alcohol for example glycerol or sorbitol.

Formulations for rectal administration may be presented as a suppository with a conventional carrier such as cocoa butter.

Formulations suitable for parenteral administration conveniently comprise a sterile aqueous preparation of the active compound which is preferably isotonic with the blood of the recipient. Such formulations suitably comprise a solution of a pharmaceutically and pharmacologically acceptable salt of oxidised thymosin β4, that is isotonic with the blood of the recipient.

Useful formulations also comprise concentrated solutions or solids containing oxidised thymosin β4, which upon dilution with an appropriate solvent give a solution for parental administration as above.

The oxidised thymosin β4 or physiologically active variant thereof disclosed herein may be administered to the lungs of a subject by any suitable means, but are preferably administered by generating an aerosol comprised of respirable particles, the respirable particles comprised of the active compound, which particles the subject inhales (i.e., by inhalation administration). The respirable particles may be liquid or solid.

Particles comprised of oxidised thymosin β4 for practising the present invention should include particles of respirable size: that is, particles of a size sufficiently small to pass through the mouth and larynx upon inhalation and into the bronchi and alveoli of the lungs. In general, particles ranging from about 0.5 to 10 microns in size (more particularly, less than about 5 microns in size) are respirable. Particles of non-respirable size which are included in the aerosol tend to deposit in the throat and be swallowed, and the quantity of non-respirable particles in the aerosol is preferably minimized. For nasal administration, a particle size in the range of 10–500 μm is preferred to ensure retention in the nasal cavity.

Liquid pharmaceutical compositions or oxidised thymosin β4 for producing an aerosol can be prepared by combining the oxidised thymosin β4 with a suitable vehicle, such as sterile pyrogen free water. Solid particulate compositions containing respirable dry particles of micronized oxidised thymosin β4 may be prepared by grinding dry oxidised thymosin β4 with a mortar and pestle, and then passing the micronized composition through a 400 mesh screen to break up or separate out large agglomerates. A solid particulate composition comprised of the oxidised thymosin β4 may optionally contain a dispersant which serves to facilitate the formation of an aerosol. A suitable dispersant is lactose, which may be blended with the oxidised thymosin β4 in any suitable ratio (e.g., a 1 to 1 ratio by weight).

Aerosols of liquid particles comprising the oxidised thymosin β4 may be produced by any suitable means, such as with a nebulizer. See, e.g., U.S. Pat. No. 4,501,729. Nebulizers are commercially available devices which transform solutions or suspensions of the oxidised thymosin β4 into a therapeutic aerosol mist either by means of acceleration of a compressed gas, typically air or oxygen, through a narrow venturi orifice or by means of ultrasonic agitation. Suitable compositions for use in nebulizers consist of the oxidised thymosin β4 in a liquid carrier, the oxidised thymosin β4 comprising up to 40% w/w of the compositions, but preferably less than 20% w/w. the carrier is typically water or a dilute aqueous alcoholic solution, preferably made isotonic with body fluids by the addition of, for example, sodium chloride. Optional additives include preservatives if the composition is not prepared sterile, for example, methyl hydroxybenzoate, antioxidants, flavouring agents, volatile oils, buffering agents and surfactants.

Aerosols of solid particles comprising the oxidised thymosin β4 may likewise be produced with an solid particulate medicament aerosol generator. Aerosol generators for administering solid particulate medicaments to a subject produce particles which are respirable, as explained above, and generate a volume of aerosol containing a predetermined metered dose of a medicament at a rate suitable for human administration. Examples of such aerosol generators include metered dose inhalers and insufflators.

For inflammation of external tissues, e.g. skin, the formulations are preferably applied as a topical ointment or cream containing the active ingredient in an amount of, for example, 0.075 to 20% w/w, preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream may include, for example, at least 30% w/w of a polyhydric alcohol, i.e. an alcohol having two or more hydroxyl groups such as propylene glycol, butane-1,3-diol, mannitol, sorbitol, glycercol and polyethylene glycol and mixtures thereof. The topical formulations may desirably include a compound which enhances absorption or penetration of the active ingredient through the skin or other affected areas. Examples of such dermal penetration enhancers include dimethylsulphoxide and related analogues.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and/or fat make up the so-called emulsifying ointment base which forms the oily dispersed phase of the cream formulations.

Emulgents and emulsion stabilizers suitable for use in the formulation of the present invention include Tween 60, Span 80, cetostearyl alcohol, myristyle alcohol, glycerol monostearate and sodium lauryl sulphate.

The choice of suitable oils or fats for the formulation is based on achieving the desired cosmetic properties, since the solubility of the active compound in most oils likely to be used in pharmaceutical emulsion formulations is very low. Thus the cream should preferably be a non-greasy, non-staining and washable product with suitable consistency to avoid leakage from tubes or other containers. Straight or branched chain, mono-or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

In addition to the aforementioned ingredients, the formulations of this invention may further include one or more accessory ingredient(s) selected from diluents, buffers, flavouring agents, binders, surface active agents, thickeners, lubricants, preservatives (including antioxidants) and the like.

The following examples describe the purification of the peptide factor and the characterisation of partially purified factor and steroid-treated monocyte supernatant. Later examples describe the characterisation of purified factor as oxidised thymosin and activity of the oxidised thymosin β4.

BRIEF DESCRIPTION OF THE DRAWINGS

The examples are described with reference to the accompanying figures, wherein:

FIG. 1 illustrates the effects of STMS on human neutrophil locomotion. Cells were tracked for 2 minutes using the computerised tracking assay method. The mean value of cell speed determined at 5 second intervals was 15.2 μm/min for speed, and extrapolated values of 1.02 $\mu m^2$/sec and 63 secs. for the diffusion coefficient and persistence respectively.

FIG. 2 illustrates the effect of supernatants from human monocytes cultured for 24 hours at 37° C., with and without $10^{-6}$M dexamethasone, on the adhesion of human neutrophils to bovine aorta endothelial cell monolayers. (a) culture medium without dexamethasone; (b) culture medium with $10^{-6}$M dexamethasone; (c) control monocyte supernatant (CMS); (d) steroid-treated monocytesupernatant (STMS). Mean±s.e.m. (vertical bars)n=3.P<0.001 given by **.

FIG. 3 illustrates the comparison of the morphology of human neutrophils treated with STMS and various neutrophil locomotion stimulators, using scanning electron microscopy. (a) $10^{-8}$M fMLP; (b) IL-8 and (c) STMS.Bar 2 μm.

FIG. 4 illustrates the comparison of the morphology of human neutrophils treated with STMS and various neutrophil locomotion stimulators and seeded on bovine aorta endothelial cell monolayers, using scanning electron microscopy. (a) $10^{-8}$M fMLP and (b) STMS. Bar 2 μm.

FIG. 5 illustrates the comparison of F-actin distribution in human neutrophils treated with STMS and various neutrophil locomotion stimulators. (a) culture medium with and without $10^{-6}$M dexamethasone; (b) $10^{-8}$M fMLP: (c)TNF; (d) STMS. Bar 2 μm.

FIG. 6 illustrates the inhibition of fMLP-induced chemotaxis of human neutrophils by STMS measured using a modified Boyden chamber assay. (a) upper chamber—culture medium with dexamethasone; lower chamber—$10^{-9}$ fMLP; (b) upper chamber—STMS; lower chamber—$10^{-9}$M fMLP; (c) upper chamber—$10^{-9}$M fMLP; lower chamber—$10^{-9}$M fMLP: (d) upper chamber—culture medium with dexamethasone; lower chamber—STMS. Number of cells which have migrated half of the mean migration distance of positive control (a). ☐ Cell-front migration distance. Five randomly selected fields were counted for each filter. Values shown are mean±s.e.m. (vertical bars)P<0.001 given by **.

Figures 7, 8A:
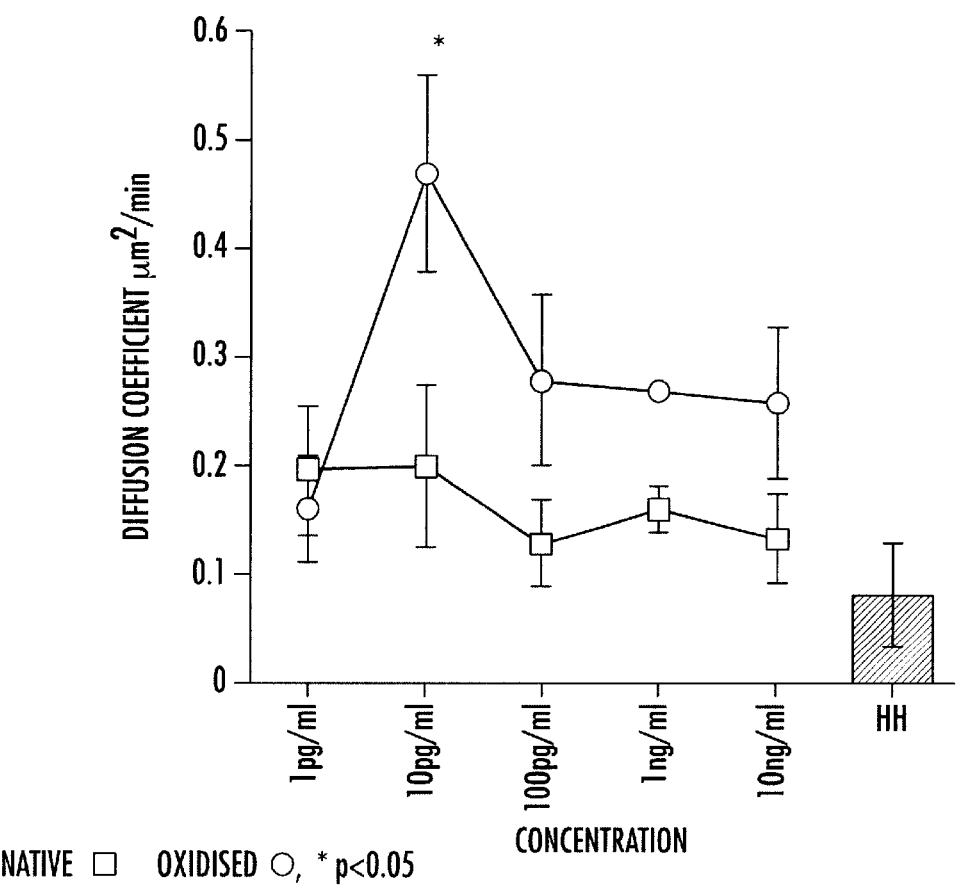
Figure 8B:
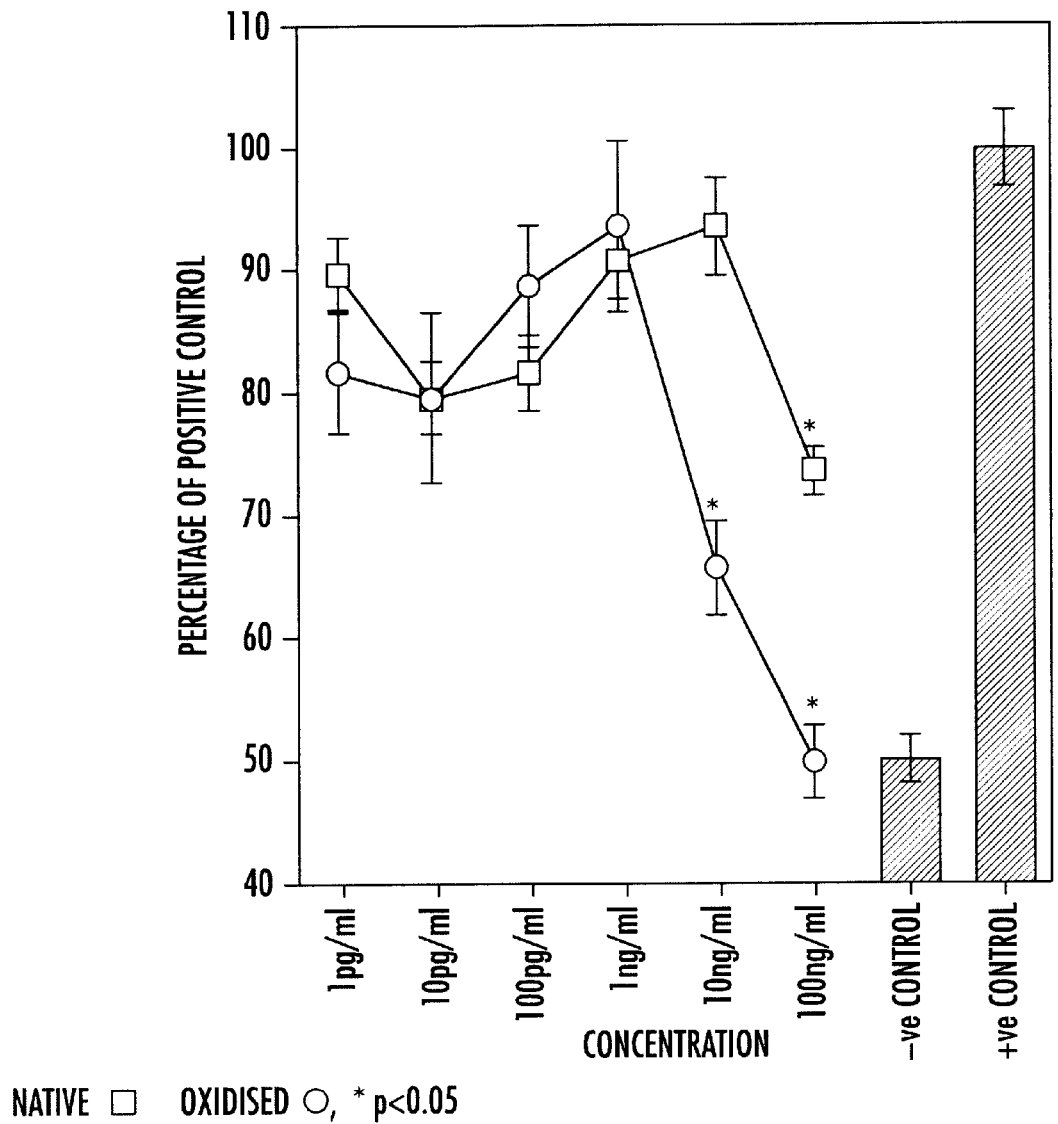
Figure 8C:
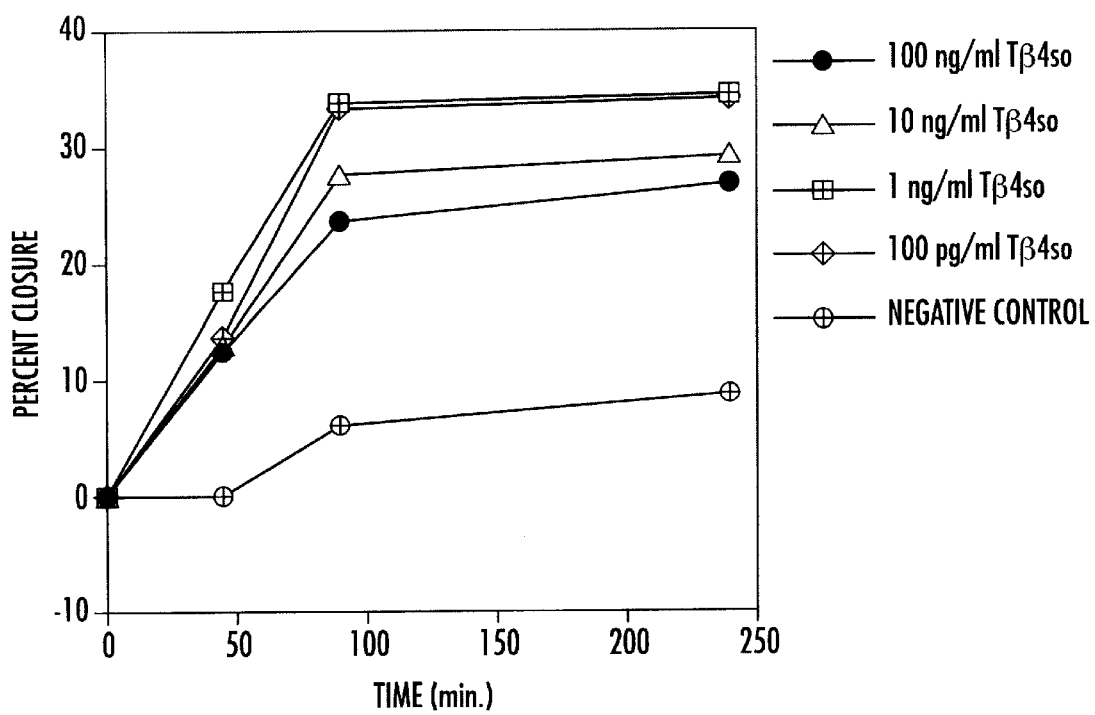
Figure 8D:
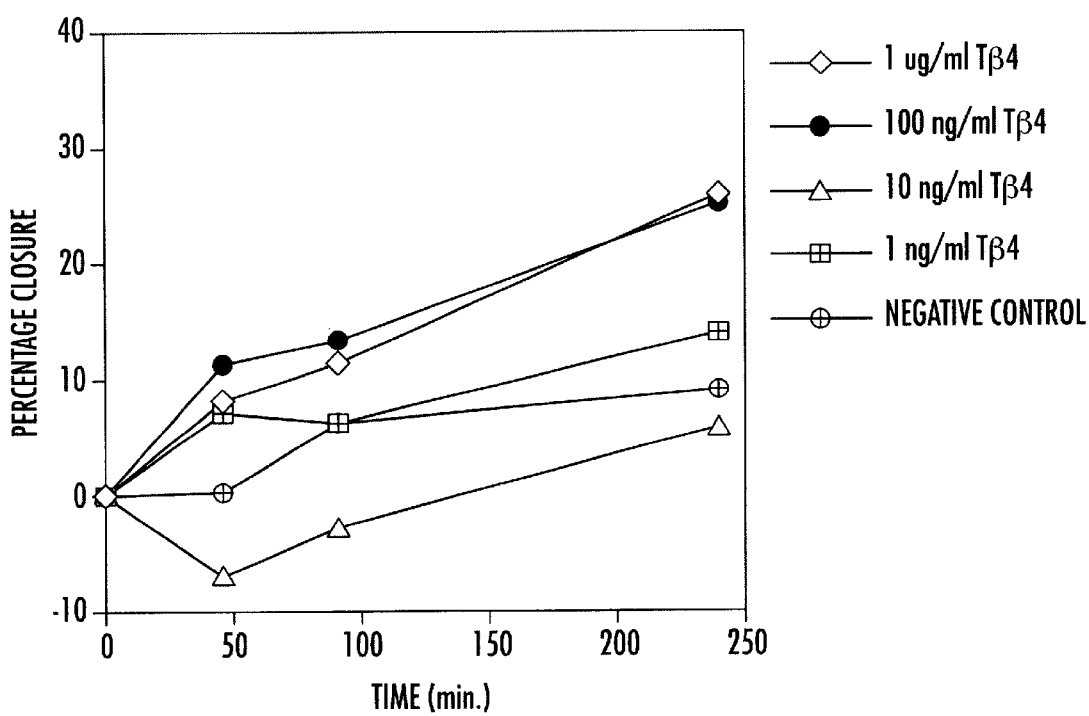

FIG. 7 shows the data for peptide 1 showing the observed ion series for low-energy CID following derivatisation with SPA. Key: Coff Collision offset (volts); Xle Leucine (Leu) or Isoleucine (Ile); Kpy Lysine epsilon-N-(3-pyridyl) acetate; Mso methionine sulphoxide; and * indicates ions observed in CID spectrum.

FIGS. 8a–d illustrate (a) dispersive locomotion of neutrophils in response to thymosin β4 (Tβ4) and oxidised thymosin β4 (Tβ4so); (b) FMLP induced chemotaxis of human neutrophils in a modified Boyden chamber is inhibited by Tβ4so to a higher degree than the non-modified peptide. A dose dependent effect was observed of inhibition of chemotaxis by Tβ4 and Tβ4so, with the oxidised peptide being tenfold more inhibitory than the native peptide; and (c) thymosin β4 sulphoxide promotes would healing in a simple scratch assay. Oxidising the methionine residue (met 6) was shown to increase the closure rate of scratch made on an endothelial monolayer on tissue culture plastic. (d) thymosin β4 promotes would healing in a simple scratch assay. Oxidising the methionine residue (met 6) was shown to increase the closure rate of scratch made on an endothelial monolayer on tissue culture plastic.

Figure 9A:
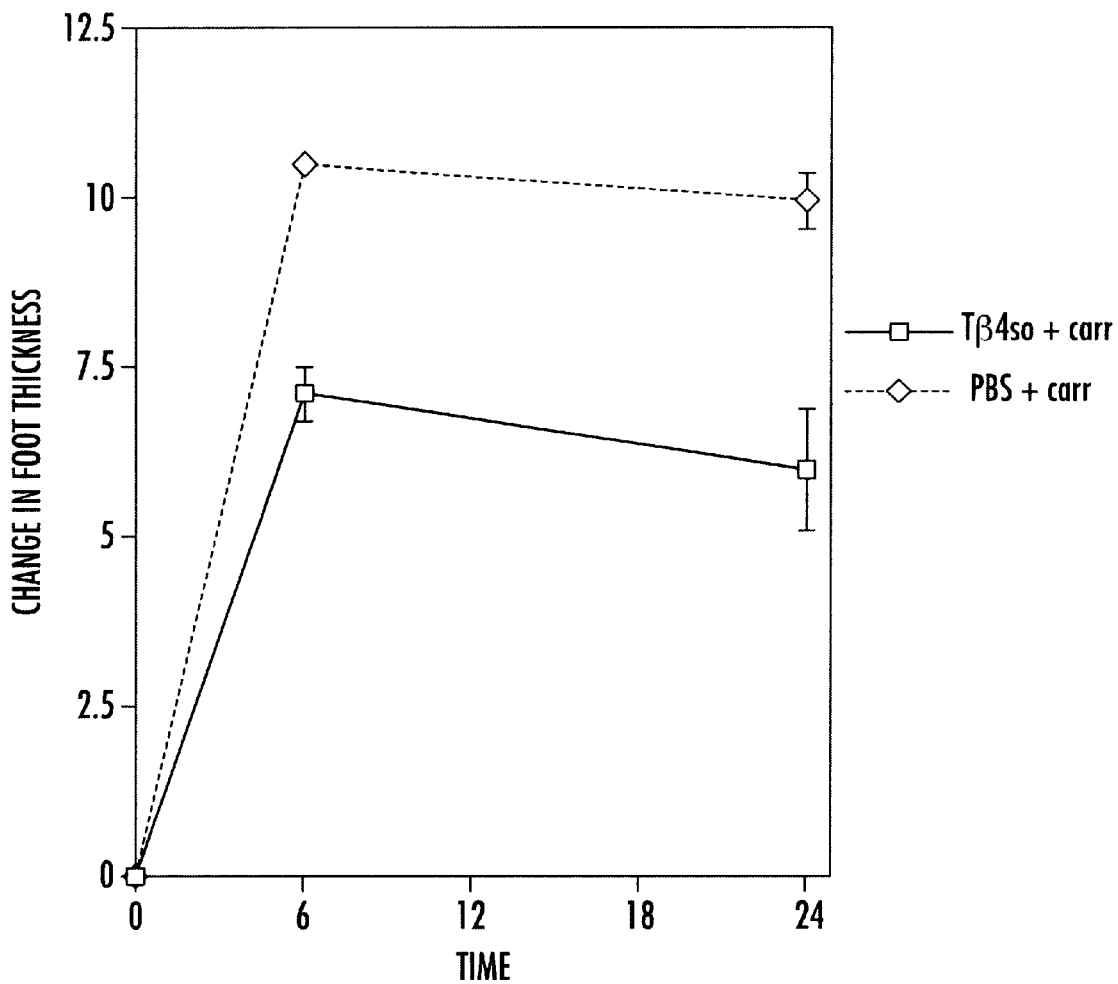
Figure 9B:
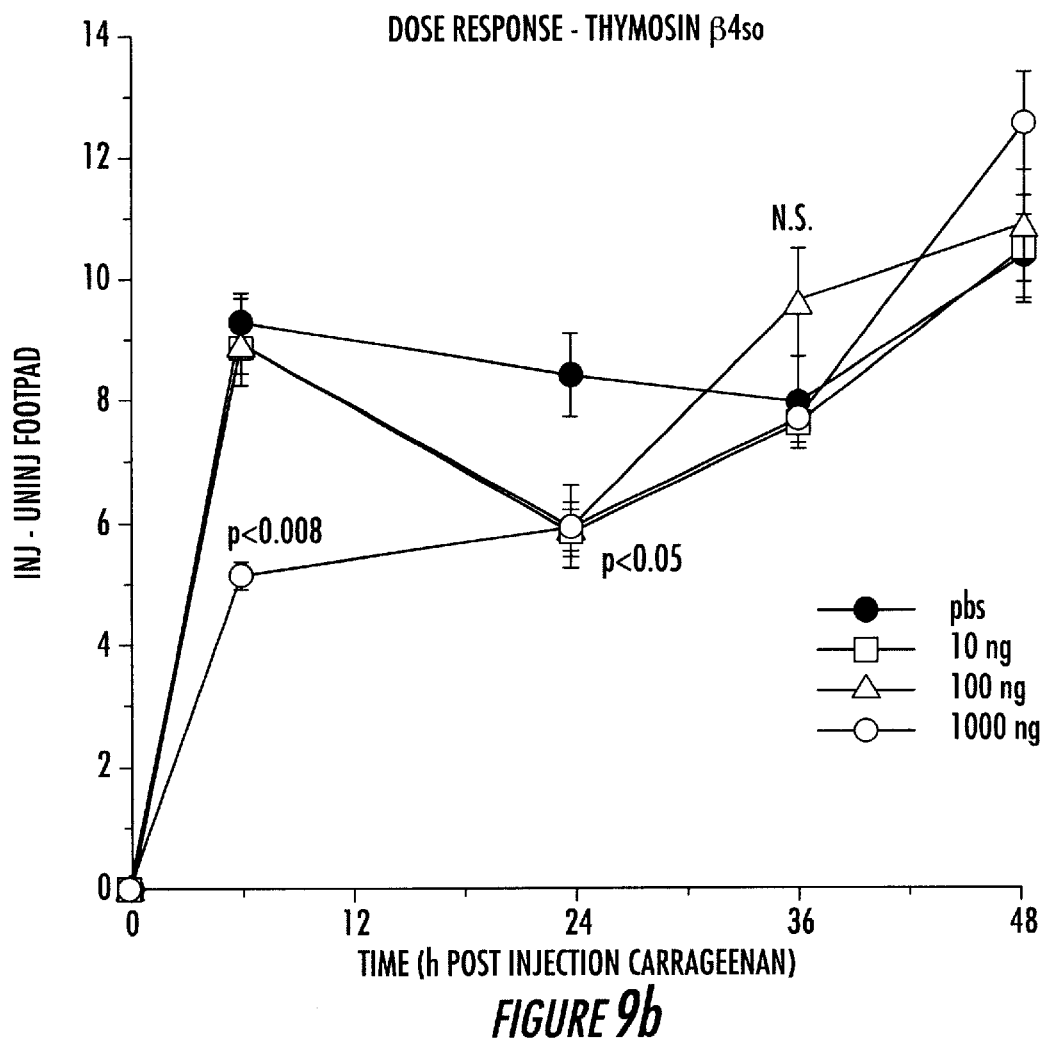
Figure 9C:
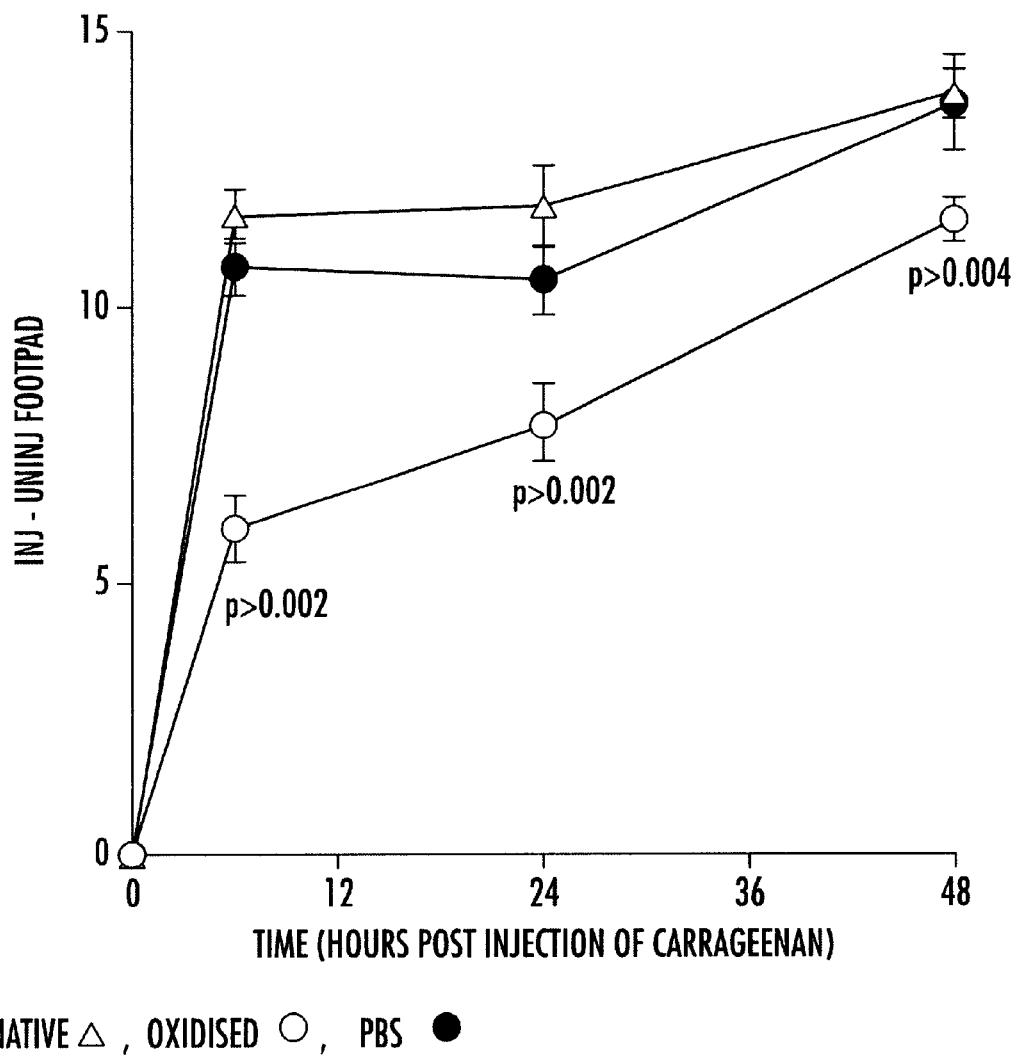

FIGS. 9a–9c show the results of assays of Tβ4 and Tβ4so in the Carrageenan induced oedema test.

EXAMPLES
Materials and Methods
Reagents

IL-8 and TNF were purchased from Genzyme, dissolved in phosphate buffered saline (PBS) and stored at 1 μg per ml at −70° C. Dexamethasone and fMLP were purchased from Sigma Chemical Co. Dexamethasone was prepared as a $10^{-2}$M stock solution in ethanol and fMLP as a $10^{-2}$M stock solution in dimethyl sulphoxide (DMSO).
Neutrophil Purification Neutrophils were obtained as described by Chettibi et al. [1993]. Briefly, whole blood was mixed with 1:10 v/v of 5% dextran and allowed to sediment at 37° C. for 1 hour. The leucocyte rich plasma was layered over Nycoprep 1.077 and centrifuged at 750 g for 15 minutes. Erythrocytes in the resulting pellet were removed by hypotonic lysis and neutrophils were washed twice with balanced salt solution (BSS). The cells were checked for viability by trypan blue exclusion (generally greater than 96% viable).
Cell Tracking Assay Automated cell-tracking migration chambers were made as previously described [Chettibi et al., 1993] and placed on the stage of an inverted phase-contrast microscope within a temperature controlled (37° C.) transparent box and locomotion observed by means of a video camera connected to a monochrome monitor and also to an Acorn A5000 computer with a Watford video digitiser programmed to capture and analyze one frame every 5 seconds. Data was obtained from a maximum of 80 selected cells and used to calculate instantaneous speed, the 2-dimensional diffusion coefficient and the locomotion persistence time, using the described procedure to eliminate the contribution of systematic drift [Chettibi et al., 1994].
Adhesion Assay Bovine aorta endothelial cells were cultured on 13 mm diameter glass coverslips in a multi-well dish in Dulbeccols modified Eagles medium with 10% foetal calf and 10% horse serum and grown to confluence. Human neutrophils suspended in BSS 0.1% bovine serum albumin (BSA) were labelled with [$^{51}$Cr]sodium chromate by incubating them at $1\times10^6$ cells/ml for 1 hour, 20 μCi/ml with periodic agitation. Free $^{51}$Cr was removed by three washes with BSS 0.1% BSA. 200 μl of neutrophils were mixed with 800 μl of STMS peptide factor or other test substances, added to the wells and incubated for 30 minutes at 37° C. Non-adherent cells were washed gently three times with BSS 0.1% BSA and coverslips were placed in a Wilj gamma counter.
Electron Microscopy Neutrophils were stimulated with various agonists for 20 minutes before fixing in 2% buffered gluteraldehyde for one hour and washed twice in PBS. Post-fixation in osmium tetroxide was followed by washing in distilled water. Uranyl acetate was then added to the samples and left in the dark for at least one hour before washing. The cells were passed through a graded series of acetone (or alcohols) ranging from 30% to dried absolute, before critical point drying and mounting.

An alternative to critical point drying was lyophilization in which, after the osmium tetroxide had been washed from the cells, they were plunged into liquid nitrogen (only suitable for cells adherent to a solid substrate). The specimens were then coated in gold and viewed in the scanning electron microscopy (SEM).
Actin Staining and Confocal Microscopy Purified neutrophils were placed on albumin-coated glass coverslips before treatment with various stimuli and incubated at 37° C. for 30 minutes. The cells were fixed in 1% paraformaldehyde solution for one hour, washed with BSS and permeabilised with 1% Triton x-100 for 15 minutes at room temperature. Cells were washed three times with BSS and treated with 0.1 mg/ml TRITC labelled phalloidin for 20 minutes at room temperature. Cells were washed three times in BSS at 5 minutes intervals and mounted on glass slides with 50% glycerol. Results were analyzed using confocal microscopy.
Chemotaxis Assay Filters (Sartorius membrane filter 3 μm pore) were cut and glued to a modified iml syringe barrel. 300 μl of $2\times10^6$/ml neutrophils were added to 300 μl antagonist and 200 μl of the suspension was added to the upper chamber (syringe barrel). The lower chamber (a 5 ml beaker), contained 3.6 ml of agonist. After 45 minutes, the cells were fixed in 70% ethanol for 5 minutes. This procedure also removes the filter from the syringe barrel by dissolving the glue. The filters were placed in a multi-well dish and treated as follows: distilled water for 2 minutes, Harris haematoxylin 1 minute, distilled water 1 min, Scotts Tap water (1:1 0.7% sodium bicarbonate:4% Magnesium sulphate (v/v) for 5 minutes, 70% ethanol 3 mins, 95% ethanol 3 minutes and 80%:20% ethanol:butanol (v/v) 5 minutes. The filters were cleared in xylene for 5 minutes, mounted in DEPEX and examined under bright field illumination with a 40× objective. Five randomly selected fields were counted for each filter.

Scratch wound assay: Human umbilical vein endothelial cells (HUVEC) were grown to confluency in multiwell dishes (Corning) and a scratch made across the diameter of each well with a sterile pipette tip. The resulting wound (approx. 1 mm) was then measured before the addition of Tβ4 or Tβ4so and at 45 min intervals.

Induction of Inflammatory Response to Carrageenin: Groups of mice were injected subcutaneously in one hind paw with 300 μg carrageenin mixed the thymosin β4, native or sulphoxide in a final volume of 50 μl. Control animals were injected with the same volume of saline. Footpad swelling was measured using a spring-dial calliper, and expressed as the difference in swelling between the carrageenin-injected paw and the uninjected, contralateral paw. The animals were injected intraperitoneally (i.p.) With the same dose of thymosin β4, native or sulphoxide and footpad measurements made at 6, 24, 48 and 72 hours.

Example 1
Preparation of Steroid Treated Monocyte Supernatant (STMS) and Partially Purified STMS Peptide Factor Steroid treated monocyte supernatant (STMS) was obtained by the culture of human monocytes which had been plated out in Hams F-10 medium at a concentration of $5\times10^7$ cells per ml in the presence of heat-inactivated 10% foetal calf serum (FCS) for 60 mins, rinsed with Phosphate buffered saline (PBS) and then cultured in the absence of FCS for 24 hours in the presence of $10^{-6}$M dexamethasone.

STMS Peptide Factor Preparation

STMS was obtained essentially as described by Chettibi et al. [1993] by the culture of human monocytes in Hams F-10 medium with 10% foetal calf serum (FCS) at a concentration of approximately $5\times10^7$ cells per ml for 60 minutes, rinsed with PBS, and then cultured without FCS for 24 hours in the presence of $10^{-6}$M dexamethasone. Parallel cultures in which dexamethasone was omitted were used to prepare control monocyte supernatant (CMS). Purification of STMS peptide factor was carried out using the 2-dimensional diffusion coefficient to identify active fraction. Partial purification was achieved using gel filtration and ion-exchange chromatography on mono-Q resin. Highly purified material was obtained by the additional use of reverse phase HPLC.

Initial sequence analysis of the peptide factor was unsuccessful because of a presumed blocked N-terminal.

These observations suggested that treatment of neutrophils with STMS induced a highly unusual mode of cytoskeletal organisation (FIG. 5d), but did not cast any direct light on the underlying basis for persistent locomotion. The apparent correlation of behaviour with adhesion under the light microscope was therefore extended by scanning EM and confocal microscopy studies.

Example 2
Biological Studies of STMS Peptide Factor

The biological interest in STMS Peptide Factor lies in its potential role as a mediator of some or all of the anti-inflammatory effects of glucocorticoids. Many preliminary observations using the supernatant as opposed to the peptide factor seemed to support this role, but others, such as the phenomenon of dispersive locomotion, were not obvious anti-inflammatory responses. However, lowered adhesiveness, which appears to be one of the underlying causes of dispersive locomotion, has clear anti-inflammatory implications.

Characteristics of Neutrophil Locomotion

Figure 2:
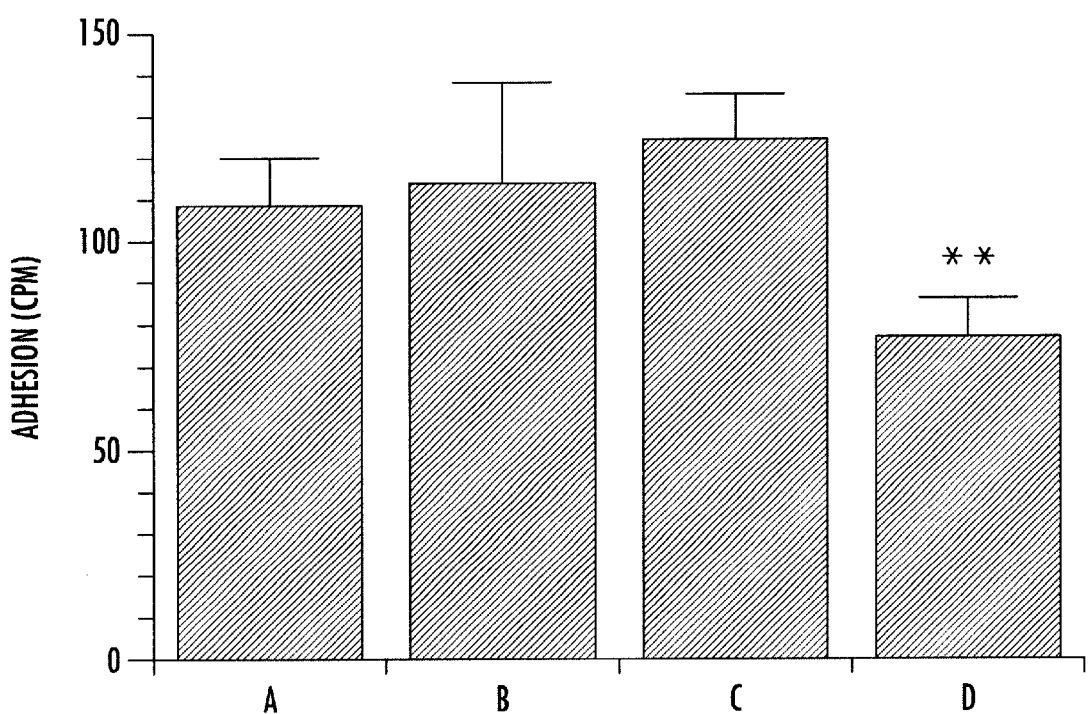

Agonists were used at concentrations which caused similar, sub-maximal stimulation of basal motility. Previous studies of crude and partially purified STMS peptide factor showed that it stimulated neutrophils to undergo highly dispersive locomotion in a uniform concentration gradient. This was in marked contrast to responses to other agents and in particular to fMLP where the locomotor characteristics. suggested that the cells, though highly motile, could not readily break their initial adhesions to the substrate. Here it is shown that partially purified STMS also produces a dispersive response at a concentration that gives a similar instantaneous speed at 10 nm fMLP (FIGS. 1,2).

In addition to the determination of quantitative locomotor parameters, observation of the cells during the assay showed very clear and characteristic patterns of behaviour when the cells were treated with different stimulating agents. Neutrophils exposed to STMS, rapidly become phase-dark corresponding to flattening and adhesion, but then regain the phase bright state and become motile. In contrast IL-8 induces characterised cyclic behaviour in which the cells darken and brighten reversibly, whilst cells treated with fMLP remain phase bright. STMS treated cells also showed a very characteristic appearance giving the subjective impression that the cell is attached to the substrate at a single site while the cell body is dynamically active above it. All other stimulants tested appeared to cause the neutrophils to form several attachment points to the substrate. This observation is consistent with previous adhesion studies which showed that STMS traced neutrophils were very readily washed off a protein-coated glass surface.

Neutrophil Polarisation and Membrane Morphology

Neutrophils treated with partially purified STMS peptide factor appeared under phase-contrast microscopy to be elongated and the characteristics of their adhesion to a protein-coated glass surface indicated that they might be attached at a single site. The cells were relatively easily detached by washing and also the appearance was suggestive of largely unattached cell body connected to the surface by an elongated process.

Scanning Electron Microscopy

Figure 3A:
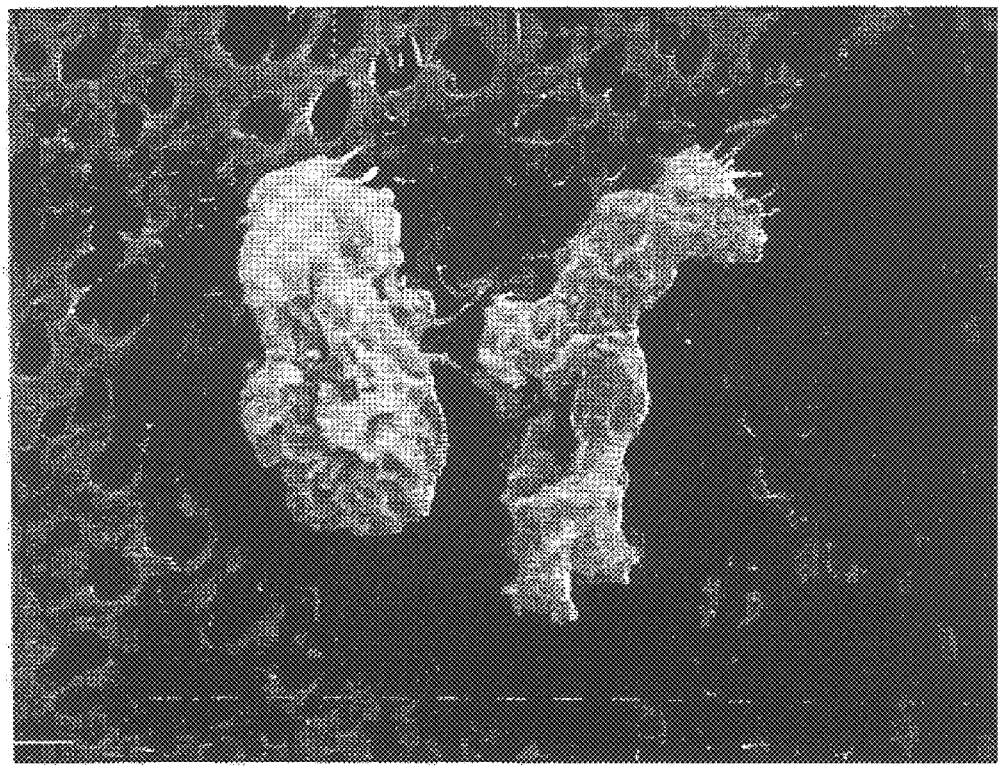
Figure 3B:
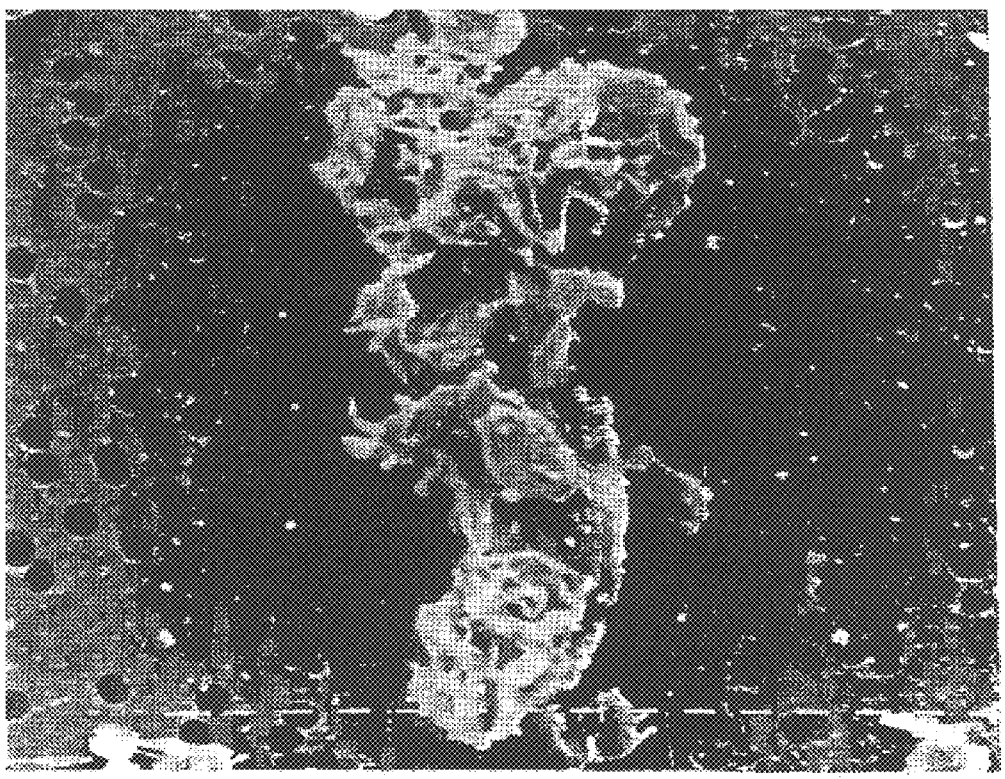
Figure 3C:
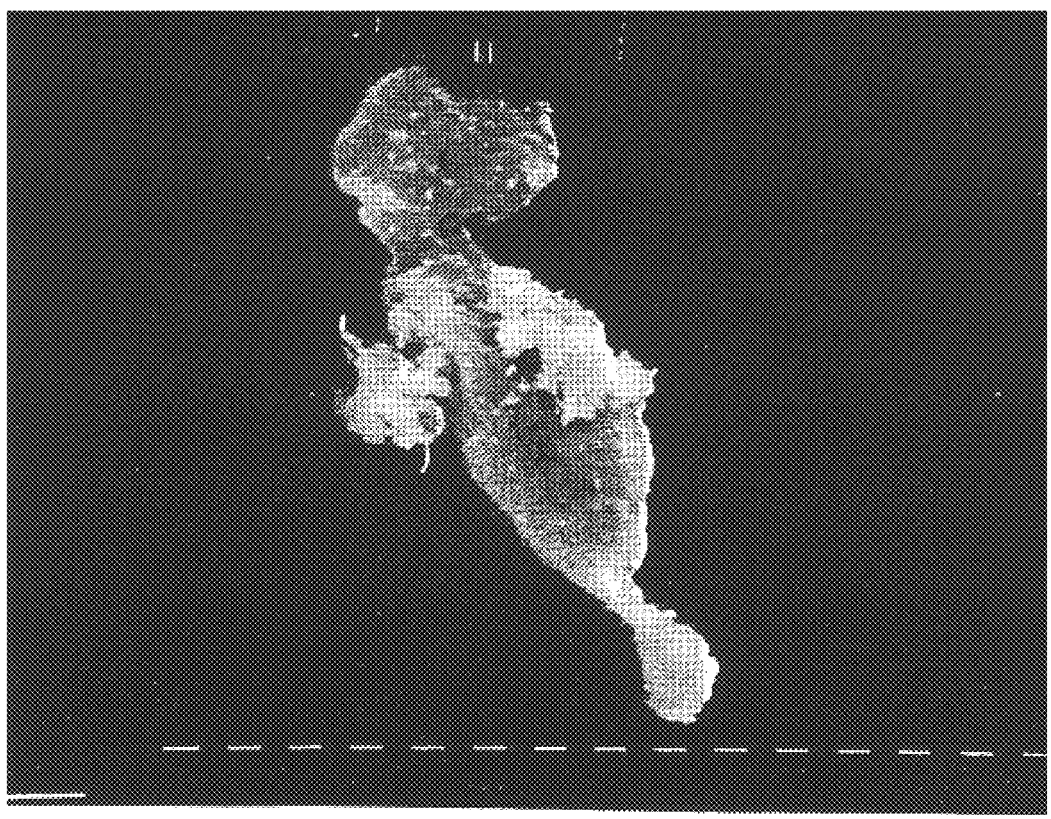

The results of this study demonstrated that cells treated with fMLP or IL-8 showed classic polarisation with abundant areas of ruffled membrane and no clear leading edge (FIGS. 3a,b,c). In addition to the ruffling shown by the apparent points of contact with the substratum, the membrane over the body of the cell was highly convoluted. Differences in the membrane induced by fMLP and IL-8, although apparent, were very hard to define. In contrast, the morphology induced by STMS was unique and readily described (FIG. 3c).

The cells were of extended bipolar shape but the two ends that appeared to be involved in adhesive contact with the substratum were not identical. The membrane was relatively smooth with numerous small protrusions and there was no very clear difference in surface appearance between the cell body and the apparent pseudopodia.

Figure 4A:
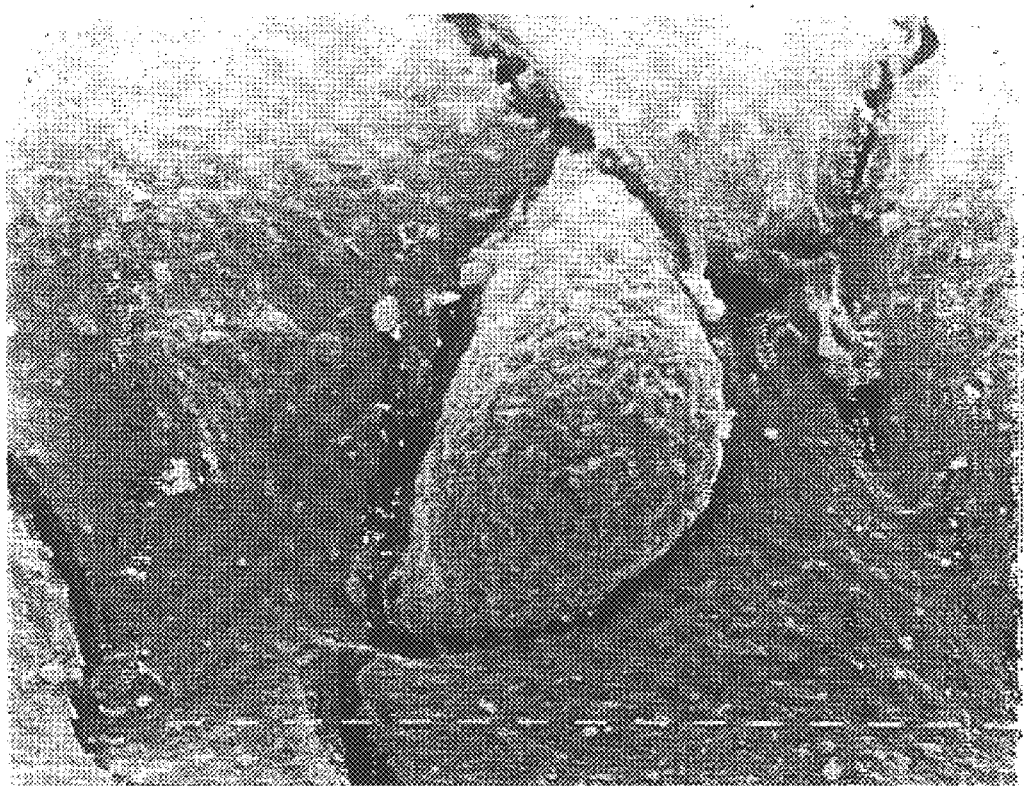
Figure 4B:
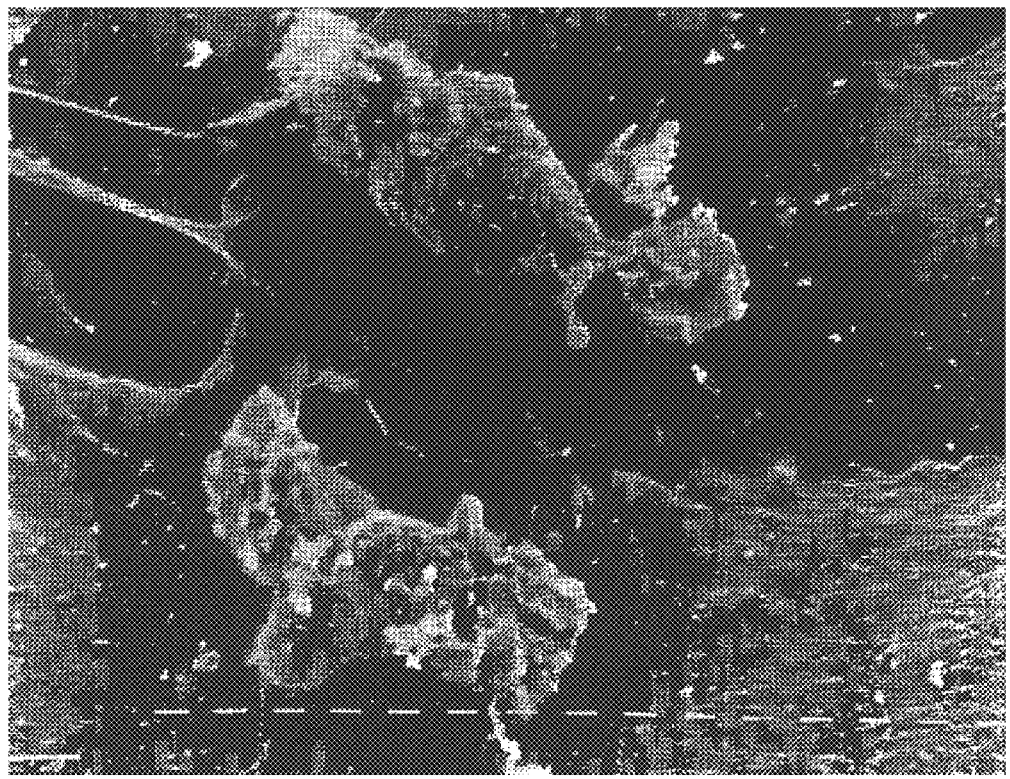

Neutrophils were seeded on bovine aorta endothelial monolayers for 30 minutes and prepared for SEM. This treatment made little difference to the appearance of the surface membrane which was ruffled in response to IL-8 and fMLP, but relatively smooth in response to STMS. The most significant difference was that whereas fMLP and IL-8 treated neutrophils were almost exclusively found at endothelial cell junctions, STMS treated cells tended to be found on the body of the endothelial cell (FIGS. 4a,b).

Confocal Microscopy

Figure 5A:
Figure 5B:
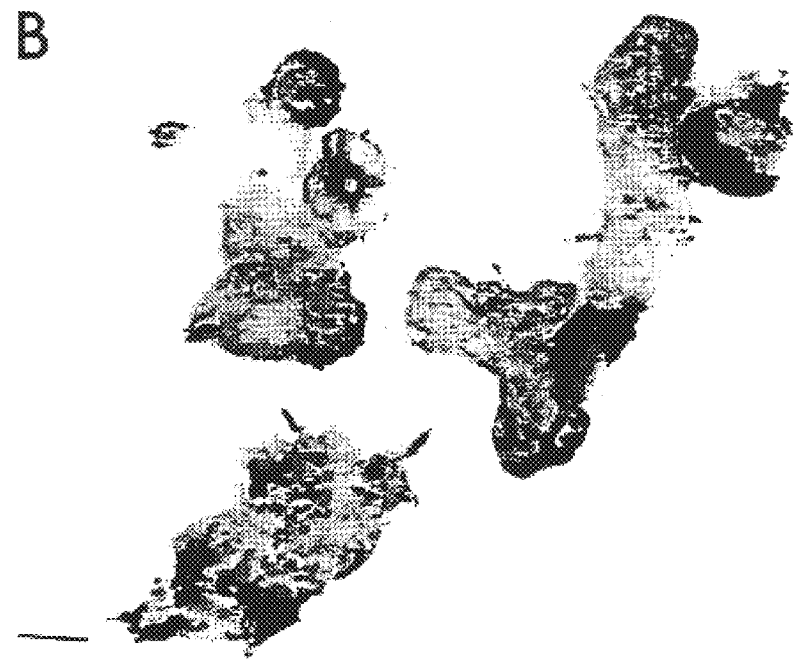
Figure 5C:
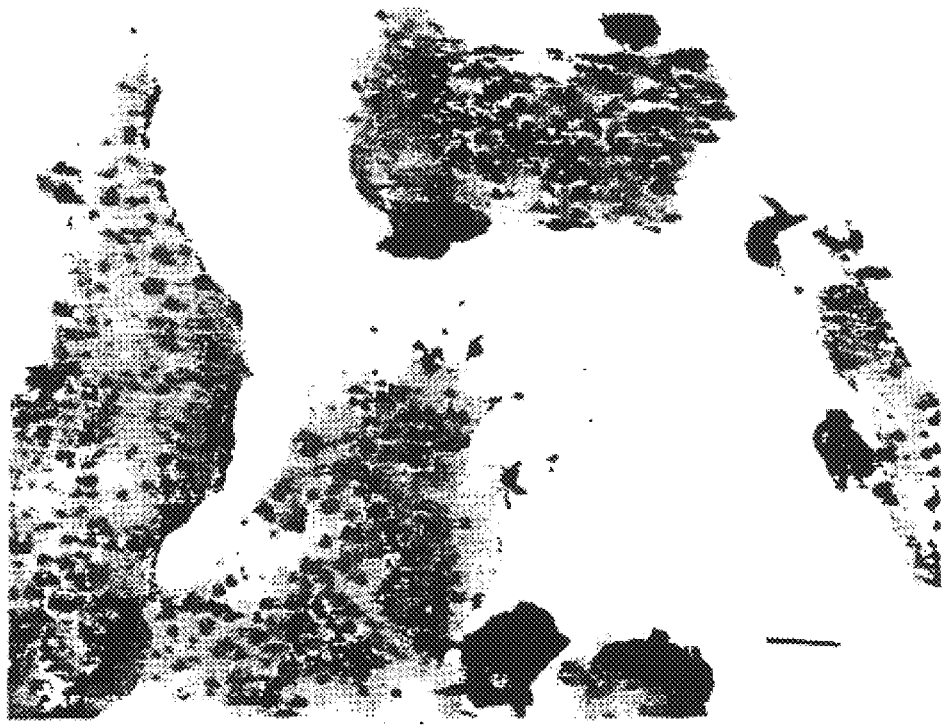
Figure 5D:
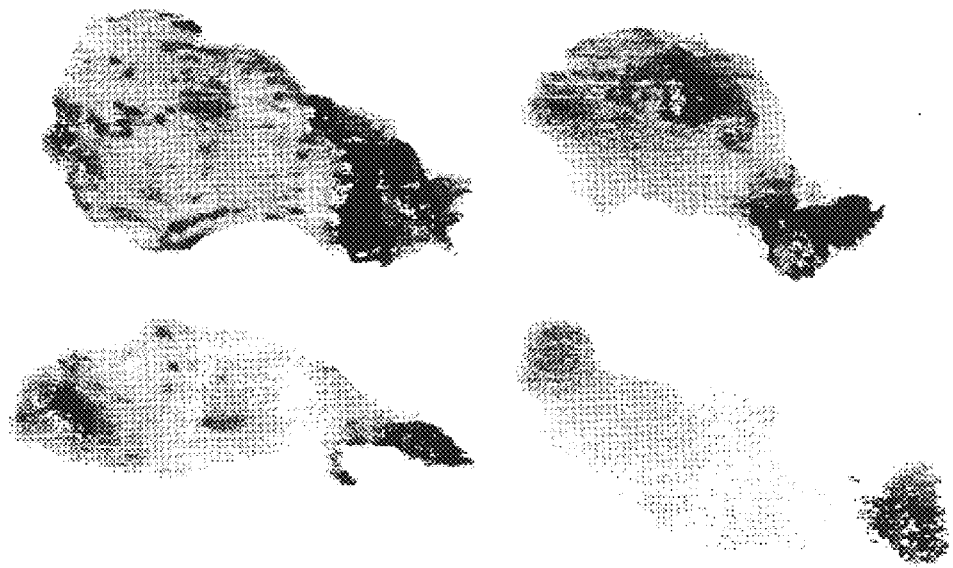

To investigate the underlying basis of the shape differences and to understand the nature of dispersive locomotion, we examined the distribution of polymerised actin in the cells. Control non-activated neutrophils showed a weak, rather punctate distribution of fluorescence, but with no sign of a major polarised focus corresponding to a relatively even distribution of cortical actin (FIG. 5a). The results obtained from fMLP were similar to those presented by other workers [Coates et al., 1992] and are consistent with the interpretation that actin polymerisation is much more intense than in control cells and is associated with points of adhesive contact that are foci of active locomotion (FIG. 5b). Cells that were highly spread in response to CMS or to TNF showed an extremely punctate distribution of F-actin (FIG. 5c). The pattern of actin staining in STMS-treated cells was highly unusual and distinct. Staining was only present in the extremes of the bipolar cells and of these two ends, which appear to be points of adhesive contact, one was invariably more intensely stained than the other (FIG. 5d).

Modulation of the Adhesion of Neutrophils to Endothelial Cells

Partially purified peptide factor reduced the adhesiveness of neutrophils to an endothelial cell monolayer. Scanning EM studies of neutrophil/endothelium interactions showed that in marked contrast to other stimuli, the supernatant peptide factor prevents adhesion and apparent invasion at endothelial cell junctions.

Inhibition of Neutrophil Secretion

Partially purified peptide factor inhibited the secretion of elastase from cytochalasin treated neutrophils (data not shown).

Example 3
Detailed Biological Studies of STMS and Peptide Factor
Neutrophil Adhesion to Bovine Aorta Endothelial Cells The previous data showing that STMS diminished neutrophil adhesion to protein-coated glass [Chettibi et al., 1993] was extended using the more physiological substrate of bovine aorta endothelial cells (FIG. 2).

Chemotaxis

Figure 6:
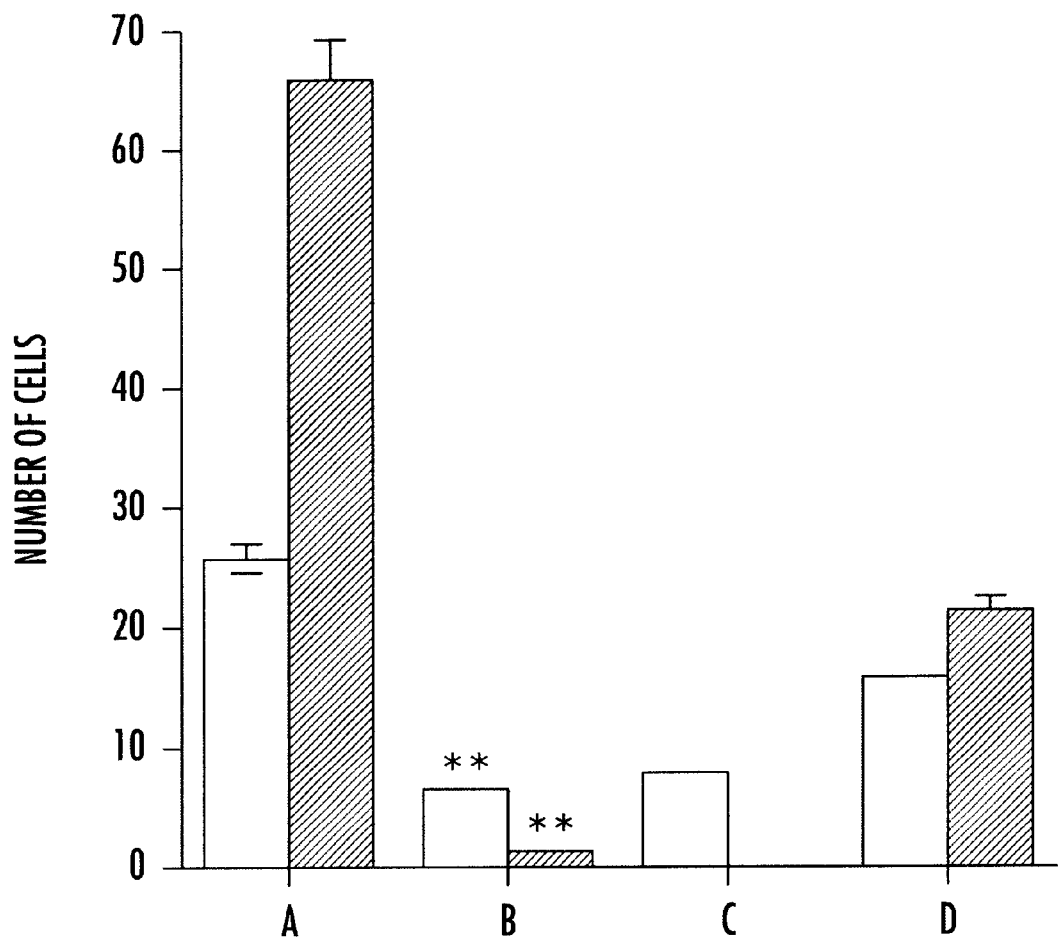

Preliminary observations of neutrophil chemotaxis using the modified Boyden chamber revealed a striking contract between the response to STMS and fMLP. Neutrophils showed massive invasion of the filter when fMLP was present in the lower chamber, but gave no such response to STMS. However when the filters were examined by the leading front method it became clear that a few STMS-treated cells were able to invade successfully, in keeping with the predictions for persistent locomotion. These observations suggested that a more suitable analysis would be to measure total invasion, or to determine the number of cells present midway between the leading front and the surface of the filter. FIG. 6 presents the analysis of chemotactic assays using both the leading front and the average invasiveness methods. The results showed that STMS was not itself chemotactic, but when present in the upper chamber, dramatically inhibited the response to fMLP. In a uniform concentration of fMLP (i.e. present in both chambers) was a marked reduction in invasiveness.

Because the production of STMS is induced by anti-inflammatory steroids, there is reason to believe that this molecule may be a true anti-inflammatory mediator. Most of the properties presented to date are consistent with a role as inhibitor of the pro-inflammatory responses of neutrophils, however its best characterised property, the induction of persistent locomotion in target cells, is by no means an anticipated anti-inflammatory response. Pro-inflammatory cytokines have a complex programme of low-dose and high-dose effects which result in an extremely varied programme of responses for cells exposed to a concentration gradient of such molecules. Many of the dynamic effects of fMLP for example, are interpreted primarily in terms of response to a concentration gradient. In contrast, the effect of STMS on neutrophils does not indicate the quantitatively distinct effects would be observed at low and high concentration gradients. The studies with uniform agonist concentrations further emphasises the critical role of concentration gradients for the chemotactic response thus although neutrophils treated with a uniform concentration of fMLP or IL-8 have highly active locomotory processes, they are unable to make effective displacement. In contrast a similar degree of locomotory activity displayed by STMS treated cells leads to a highly effective locomotion.

It is well established that actin polymerisation is an early response to stimulation of neutrophils by TMLP. Coates et al. [1992] have provided evidence that actin polymerisation is the early and dominant event in determining shape changes and dictating the specific patterns of polarisation. The link between the fMLP receptor and these early membrane events is believed to be provided by protein kinase C (PKC) activation that then leads to activation of the small cytosolic GTP-binding proteins [Ridley, 1994].

In addition the role of PKC in the phosphorylation of MARCKs and the dynamic role of phosphorylation and calcium binding. in determining the cyclic interaction of actin filaments with the plasma membrane has been recently reviewed by Janmey, [1995]. The present observations suggest that actin based locomotory processes are in competition around the cell periphery and only lead to productive displacement if an agonist gradient causes unequal activity of such processes at the leading edge of the cell. An alternative model is that the role of the gradient is primarily to weaken adhesions at the tail of the cell.

The pattern of responses to STMS is unusual in many important respects. The actin pool appears to be highly dynamic, but the distribution of F-actin is mainly constrained to one end giving a unipolar distribution of actin in a bipolar cell. The membrane over most of the cell body remains relatively smooth and this lack of ruffling was observed both with cells in suspension and on the surface of cells stuck (albeit loosely) to the endothelium. Interestingly, the lack of ruffles may manifest itself in the inability of these neutrophils to discern the gaps between endothelial cells, thereby inhibiting an inflammatory response.

The data obtained in the tilt assay, where cell locomotion is highly polarised by a gravitational field, show that the active cells always maintain one point of stable adhesion with the substrate. It therefore follows that to maintain this polarity the bulk of the polymerised actin must cycle repeatedly from one end of the cell to the other. This pattern of activity does tend to suggest that the dipolarity of the cell is determined by a pre-existing structural feature, as yet uncharacterised.

One of the most important aspects of the behaviour of STMS peptide factor as an anti-inflammatory mediator is its modulation of cell responses to pro-inflammatory mediators. This has been tested in the above work using motility stimulation as the basic parameter for comparison of activities. Under conditions where STMS and fMLP or IL-8 are equipotent as locomotion simulators, the morphological, adhesive and locomotor responses to STMS tend to dominate and the cells remain phase-bright, bipolar and undergo dispersive locomotion.

Of even greater significance, STMS Peptide Factor, which is not itself chemotactic, is able to suppress the chemotactic response to fMLP. It is of interest here to discuss the role of persistence in chemotaxis. By the very nature of the concept, any form of directed locomotion has persistence. This is seen most clearly in the case of the tilt assay [Chettibi et al., 1994] where the response to STMS showed more than 90% directional movement and the persistence although infinite, became an essentially meaningless concept. For locomotion in a uniform concentration of STMS, persistence reflects some kind of inertia in the locomotor system. Bearing in mind the low Reynolds number conditions, this inertia must relate to the organisation of the structure on which the cytoskeleton acts or redistributes itself during locomotion.

The electron micrographs of STMS-treated cells on an endothelial layer show firstly that the cells do not seek the junctions between endothelial cells or do not have suitable exploratory leading lamellae to penetrate such a gap if encountered.

It can be concluded that persistence of neutrophil locomotion caused by steroid-induced factor results from an effect on actin distribution and polymerisation. This type of locomotion appears to render neutrophils resistant to chemotactic stimuli and impairs their ability to adhere to endothelial cells and to migrate through endothelial cell junctions. As such this factor appears to be an important mediator of anti-inflammatory glucocorticoid action and pure peptide factor may be effectively used in place of steroids for therapy of chronic inflammatory conditions.

Example 4

Identification of Active Factor

STMS (Steroid Treated Monocyte Supernatant) was defined as an activity in the culture medium from steroid treated human monocytes that influenced the motility of human neutrophils, specifically to give dispersive or persistent locomotion characterised by a high 2-dimensional diffusion coefficient.

The material described by Dr Chettibi et al. was highly purified by a combination of ion-exchange and gel filtration steps, but the critical procedure was reverse phase HPLC using an HPLC columnand an elution gradient made from
A) 0.1% trifluoroacetic acid
B) 0.1% trifluoroacetic acid in 50% acetonitrile
The activity eluted at or around 34% B.

Separation methods involving extremes of pH or ionic strength profoundly changed the dose-response curve.

The most active material prepared by this method is light pink in concentrated solution and was characterised by an elution trace showing an absorption peak at 214 nm with a distinct shoulder. Further resolution was not possible and neither could the activity be attributed to the peak or the shoulder. Mass spectroscopy showed a single major component of mass 1331 Da and fragmentation analysis gave species of 1186 Da and 991 Da. Full analysis (Dr Pappin ICRF) confirmed that the major peak was acyanocobalmin, a derivative of vitamin $B_{12}$. It was surmised that vitamin $B_{12}$ may in fact be a contaminant or serving to mask the actual peptide factor. Preparation of STMS and subsequent purification of the peptide factor was therefore conducted omitting vitamin $B_{12}$. It was at this time that it was discovered that cells responded to material eluting from HPLC with a concentration optimum that was at least $10^4$-fold lower than the concentration present in culture medium. These observations suggested that the active factor was a complex of a small molecule with a carrier protein.

Preparation of STMS undertaken omitting vitamin $B_{12}$ from the medium resulted in a high yield of activity. This was purified using force dialysis (in vacuo) to concentrate 500 ml of culture medium to less than 20 ml. The dialysand was washed with 2 changes of distilled water. The sample was then purified by absorption and elution from Mono Q anion exchange resin and gel filtration on the Pharmacia peptide column run at high salt concentration. The sample was then subjected to purification by reverse phase HPLC as above. The most highly purified material eluted as a single peak and was non-pigmented.

Mass spectroscopic analysis now revealed a single major peak of average mass 4980 Da (+/−2 Da). Mass measurement following esterification of a small portion of the peptide material indicated the presence of 11 acidic amino acid residues (Aspartic and Glutamic acid).

Peptide was then digested with 100 ng trypsin (Boehringer, modified) in 6 µl 50 mM ammonium bicarbonate (pH 7.8) containing 15% V/V n-propanol 0.5% hexyl-B-glucopyranoside (HBG) overnight at 25° C. The digested peptides were then reacted with N-succinimidyl-2(3-pyridyl)acetate (SPA) in order to enhance b-ion abundance and facilitate sequence analysis by tandem mass spectrometry (Sherman et al., 1995). Dried peptide fractions were treated with 7 µl 1% w/v N-succinimidyl-2(3-pyridyl) acetate in 0.5M HEPES (pH 7.8 with NaOH) containing 15% v/v acetonitrile for 20 min on ice. The reaction was terminated by 1 µl heptafluorobutyric acid (HFBA) and the solution immediately injected onto a capillary reversephase column (300 um×15 cm) packed with POROS R2/H material (Perseptive Biosystems, MA) equilibrated with 2% v/v acetonitrile/0.05% v/v TFA running at 3 µl/min. The adsorbed peptides were washed isocratically with 10% v/v acetonitrile/0.05% v/v TFA for 30 minutes at 3 µl/min to elute the excess reagent and HEPES buffer. The derivatised peptides were then eluted with a single step gradient to 75% v/v acetonitrile/0.1% v/v formic acid and collected in a single 4 µl fraction. Five derivatised peptides were then fully sequenced by low-energy collision-induced dissociation (CID) using a Finnigan MAT TSQ7000 triple quadrupole MS fitted with a nanoelectrospray source (Hunt et al., 1986; Wilm and Mann, 1996). CID was performed using 2–3 mTorr argon with collisional offset voltages between −13V and −33V. The product-ion spectra were collected with Q3 scanned at 500 amu/sec.

The 5 sequences obtained were:
1) Ac-SDKPDMAE[LI]EKFDK Ac-acetyl; Met oxidised to the Met-sulphoxide (+16 Da)
2) TETQEK
3) NP[LI]PSK
4) ET[LI]EQEK
5) QAGES Free-Acid at C-terminus The data identifying peptide 1 and confirming that the methionine was oxidised to the met-sulphoxide are shown in FIG. 7.

Note: Cannot distinguish between Leu and Ile [LI] as they are isomers. Sequences corresponded exactly to tryptic fragments of human Thymosin Beta-4.

Thymosin β4 was now prepared from human neutrophils by the method of (Hannapell et al 1982) which used HPLC purification of the perchloric acid supernatant. Four major peaks were obtained and analysed by mass spectroscopy. The identification of two of these peaks was confirmed as Thymosin β4 (the major peak) eluting at 37% B and oxidised thymosin β4 eluting at 34% B. Two other peaks gave no MW signatures.

Thymosin β4 was also synthesised by Dr Pappin but the final product had an unidentified modification believed to lie in the C-terminal serine.

We now attempted to oxidise the thymosin β4 using hydrogen peroxide and with the HPLC elution pattern as the assay. Treatment of thymosin β4 with H O (50 vol.) for five minutes at room temperature gave virtually quantitative conversation.

Dr Pappin showed this molecule to have average mass 4980 Da (+/−2 Da).

Example 5

The activity of Tβ4so, in the neutrophil locomotion assays showed Tβ4so as being dispersive at low concentrations and stimulating non-dispersive locomotion above a concentration optimum, FIG. 8a. Native Tβ4 did not give significant dispersive locomotion in these assays. Neutrophil locomotion assays are notoriously hard to standardise and we therefore attempted to confirm the identity of the factor using an independent assay, the inhibition of chemotaxis. Earlier work had shown that STMS inhibited neutrophil chemotaxis to fMLP (Young et al 1997). We now measured the activities of Tβ4 and Tβ4so, in the Boyden Chamber assay and showed that neither was chemotactic, but both inhibited chemotaxis to fMLP, with the oxidised form being an order of magnitude more potent, FIG. 8b. These results provided grounds to believe that Tβ4so might be the biologically active extracellular form of Tβ4 and we investigated this by comparing the activity of the two species in the endothelial sheet wound closure test, one of the more accessible bioassays for Tβ4 activity (Malinda et al 1997). The results for the effect of Tβ4 were in close agreement with published data, but Tβ4so was active with at least an order of magnitude higher potency than the native peptide, FIG. 8c. In view of the contamination of the native Tβ4 with the more active oxidation product (7% in this case), the present results are consistent with the hypothesis that Tβ4so is the sole biologically active species. In further studies HPLC purified Tβ4 was dried and stored under nitrogen at −20° C. and dissolved immediately before use. These results, and in particular the inhibition of chemotaxis, gave reason to believe, that Tβ4so could attenuate neutrophil associated inflammatory processes, so the in vitro observations were extended in vivo using the carrageenan-induced inflammation model, which is characterised by massive neutrophil infiltration with accompanying oedema formation (Ianaro 1994). Administration of Tβ4so 30 minutes prior to, during and 6 hours after hind footpad injection of carrageenan into BALB/c mice induced significant suppression of swelling, which was evident after 6 h and sustained up to 24 hours (FIG. 9a). Suppression was dose responsive and specific, since administration of 10 or 100 ng doses of Tβ4so, or of PBS of Tβ4 (1000 ng) was ineffective (FIG. 9b) A comparison between 800 ng doses of Tβ4so and Tβ4 was carried out in this assay and clearly showed that only the oxidised peptide significantly reduced carrageenan-induced oedema (FIG. 9c). These data clearly indicated that methionine oxidation was critical to achieve in vivo anti-inflammatory activity of Tβ4so, and strongly supported the biological plausibility of the in vitro findings.

REFERENCES

Almawi, W. Y., Lipman, M. L., Stevens, A. C., Zanker, B., Hardo, E. T. and Strom, T. B. (1991): Abrogation of glucocorticosteroid-mediated inhibition of T cell proliferation by the synergistic action of IL-1, IL-6 and TNFγ. J. Immunol. 146, 3523–3527.

Arnaout, M. A. (1993): Dynamics and regulation of leukocyte-endothelial cell interactions, Curr. Opin. Haematol. 1,113–122.

Bevilacqua, M. P. and Nelson, R. M. (1993). Selectins. J. Clin. Invest. 91. 379–387.

Chettibi, S., Lawrence, A. J., Stevenson, R. D., and Young, J. D. (1993): A factor released by monocytes in the presence of dexamethasone stimulates neutrophil locomotion. Br.J.Pharmacol. 108.248–254.

Chettibi, S., Lawrence, A. J., Young, J. D. Lawrence, P. D. and Stevenson, R. D. (1994): Dispersive locomotion of human neutrophils in response to a steroid-induced factor from monocytes. J.Cell Sci. 107.3173–3181.

Coates, T. D., Watts, T. G. Hartman, H. and Howard, T. H. (1992): Relationship of F-actin distribution to development of polar shape in human polymorphonuclear neutrophils. J.Cell Biol. 117.765–774.

Cronstein, B. N., Kimmel, S. C., Levin, R. I., Martinuik, F. and Weissmann, G. (1992): A mechanism for the anti-inflammatory effects of corticosteroids. The glucocorticoid receptor regulates leukocyte adhesion to endothelial cells and expression of endothelial leukocyte adhesion molecule-1 and intercellular adhesion molecule-1. Proc. Nat. Acad. Sci USA 89.9991–9995.

Flower, R. J. (1990): Lipocortin. In Cytokines and lipocortins in inflammation and differentiation, pp. 11–25. New York: Wiley-Liss.

Goulding, N. J., Gogolphin. J. L. M Sharland, P. R., Peers, S. H., Sampson, M., Maddison, P. J. and Flower, R. J. (1990): Anti-inflammatory lipocortin 1 production by peripheral blood leucocytes in response to hydrocortisone. Lancet 335, 1416–1418.

Hannapell E., Davoust S., Horecker D. L., (1982) "Isolation of peptides from calf thymus". Biochem. Bisphys. Res. Commun. Vol.104 p266–271.

Hogg, N., and Berlin, C. (1995): Structure and function of adhesion receptors in leukocyte trafficking. Immunology today 16, 327–330.

Hunt, D. F., Yates, J. R., Shabanowitz, J., Winston, S. and Hauer, C. R. (1986) Protein sequencing by tandem mass spectrometry. Proc. Natnl. Acad. Sci. USA 84, 6233–6237.

Ianaro, A., O'Donnell, C. A., Di Rosa, M., & Liew, F. Y. A nitric oxide synthase inhibitor reduces inflammation, downregulates inflammatory cytokines and enhances interleukin-10 production in carageenan induced oedema in mice. Immunology, 32, 370–375 (1994).

Jamney, P. A. (1995): Phosphoinositides and calcium as regulators of cellular acting assembly and disassembly. Ann Rev. Physiol. 56, 169–191.

Kwon, O. J., Collins, P. D., Au, B., Adcock, I. M., Yacoub, M., Chung, K. F., Barnes, P. J. (1993): Glucocorticosteroid inhibition of TNF-Alpha-induced IL-8 gene expression in human primary cultured airway epithelial cells. American rev. resp. dis., 147.

Lew, W., Oppenheim, J. J. and Matsushima, K. (1988): Analysis of the suppression of IL-1α and IL-1β production in human peripheral blood mononuclear adherent cells by a glucocorticoid hormone. J. Immunol. 140, 1895–1902.

Malinda, K. M., Goldstein, A. L. & Kleinman, H. M. Thymosin β4 Stimulates Directional Migration of Human Umbilical Vein Endothelial Cells. FASEB J. 11: 472–481 (1997).

Ridley, A. J. (1994): Membrane ruffling and signal transduction. Cold Spring Harbour Symposia on Quantitative Biology 16,321–327.

Sherman, N. E., Yates, N. A., Shabanowitz, J., Hunt, D. F. Jeffery W., Bartlet-Jones, N. and Pappin, D. J. C. (1995). A novel N-terminal derivative designed to simplify peptide fragmentation. Proceedings of the 43rd ASMS Conference on Mass Spectrometry and Allied Topics, Atlanta, Ga., May 21–26, page 626–627.

Standiford, T. J., Kunel, S. L., Rolfe, M. W., Evanoff, H. L., Allen, R. M. and Strieter, R. M. (1992): Regulation of human alveolar macrophage and blood monocyte derived interleukin-8 by prostaglandin E2 and dexamethasone. Am.J.Respir.Cell.Mol.Biol.6,75–81.

Stevenson, R. D. (1973): Hydrocortisone and the migration of human leucocytes: an indirect effect mediated by mononuclear cells. Clin. Exp. Immunol.14,417–426.

Stevenson, R. D. (1974): Polymorph migration stimulator, a new factor produced by hydrocortisone-treated monocytes. Clin. Exp. Immunol. 17.601–606.

Stevenson, R. D. (1978). Stimulation of capillary tube polymorph migration: an indirect glucocorticoid effect on microtubular function. Clin. Exp. Immunol.33,478–485.

Stossel, T. P. (1988): The mechanical responses of white blood cells. In Inflammation: Basic principles and clinical correlates (ed. J. I. Gallin, I. M. Goldstein and R. Snyderman), pp. 325–342. Raven Press, New York. Wilm, M. and Mann, M. (1996). Analytical properties of the nanoelectrospray ion source. Anal. Chem. 68, 1–8.

Wong, W. T., Frost, S. C. and Nick, H. S. (1991): Protein-synthesis dependent induction of annexin 1 by glucocorticoid. Biochem. J. 275,313–319.

Young, J. D., MacLean, A. G., Lawrence, A. J., Stevenson, R. D. & Chettibi, S. Relationship of human neutrophil morphology and actin distribution to dispersive locomotion caused by a steroid induced factor. Experimental Biology Online. 2,7 (1997).

What is claimed is:

1. A method of treating an inflammatory condition in a subject comprising administering an oxidised thymosin β4, physiologically active variant, or salt thereof.

2. The method according to claim 1 wherein the inflammatory condition is due to a inflammatory arthropathy, connective tissue disease, vasculitic syndrome, respiratory disease, dermatological disease, gastrointestinal disease, haematological disease, transplantation/prosthetic rejection or infection.

3. The method according to claim 1 wherein the inflammatory condition is a result of a separate drug therapy.

4. A method of treating sepsis in a subject comprising administering a therapeutic amount of an oxidised thymosin β4, physiologically active variant, or salt therof.

* * * * *